United States Patent
Ootsuki

(10) Patent No.: US 10,537,389 B2
(45) Date of Patent: Jan. 21, 2020

(54) SURGICAL SYSTEM, IMAGE PROCESSING DEVICE, AND IMAGE PROCESSING METHOD

(71) Applicant: SONY CORPORATION, Tokyo (JP)

(72) Inventor: Tomoyuki Ootsuki, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 6 days.

(21) Appl. No.: 15/566,776

(22) PCT Filed: May 12, 2016

(86) PCT No.: PCT/JP2016/064083
§ 371 (c)(1),
(2) Date: Oct. 16, 2017

(87) PCT Pub. No.: WO2016/190113
PCT Pub. Date: Dec. 1, 2016

(65) Prior Publication Data
US 2018/0098812 A1 Apr. 12, 2018

(30) Foreign Application Priority Data

May 26, 2015 (JP) .................................. 2015-106419

(51) Int. Cl.
*A61B 3/00* (2006.01)
*A61B 34/10* (2016.01)
(Continued)

(52) U.S. Cl.
CPC ............ *A61B 34/10* (2016.02); *A61B 3/0025* (2013.01); *A61B 3/102* (2013.01); *A61B 3/113* (2013.01);
(Continued)

(58) Field of Classification Search
None
See application file for complete search history.

(56) References Cited

U.S. PATENT DOCUMENTS

| 2009/0131921 A1 | 5/2009 | Kurtz et al. |
| 2014/0188093 A1 | 7/2014 | Kurtz et al. |

(Continued)

FOREIGN PATENT DOCUMENTS

| JP | 2010-538700 A | 12/2010 |
| JP | 2012-152469 A | 8/2012 |

(Continued)

OTHER PUBLICATIONS

International Search Report dated Aug. 9, 2016 in PCT/JP2016/064083.

*Primary Examiner* — Delomia L Gilliard
(74) *Attorney, Agent, or Firm* — Xsensus LLP

(57) ABSTRACT

The present technology relates to a surgical system, an image processing device, and an image processing method capable of obtaining the posture of an eye more firmly and with a high degree of accuracy.

An image information acquisition unit acquires a tomographic image that is a cross-sectional image taken in a direction substantially parallel to an eye axis direction of an eye of a patient. An image recognition unit recognizes each part of the eye on the tomographic image by means of image recognition on the basis of the tomographic image. The control unit calculates the posture of the eye on the basis of the result of recognition of each part of the eye. In this way, by recognizing each part of the eye on the basis of the tomographic image and calculating the posture of the eye on the basis of the result of recognition, the posture of the eye can be obtained more firmly and with a high degree of accuracy. The present technology can be applied to a surgical system.

19 Claims, 23 Drawing Sheets

(51) Int. Cl.
  *A61B 90/25* (2016.01)
  *A61B 3/10* (2006.01)
  *A61B 3/113* (2006.01)
  *A61B 3/14* (2006.01)
  *A61F 2/16* (2006.01)
  *A61B 90/00* (2016.01)
  *A61F 9/007* (2006.01)

(52) U.S. Cl.
  CPC .............. *A61B 3/14* (2013.01); *A61B 90/25* (2016.02); *A61F 2/1662* (2013.01); *A61B 2034/107* (2016.02); *A61B 2090/3735* (2016.02); *A61F 9/00745* (2013.01)

(56) References Cited

U.S. PATENT DOCUMENTS

| | | |
|---|---|---|
| 2014/0205169 A1 | 7/2014 | Yamakawa et al. |
| 2015/0116725 A1* | 4/2015 | Lemonis ............ A61F 9/00802 356/479 |
| 2015/0328045 A1 | 11/2015 | Kurtz et al. |
| 2016/0135683 A1* | 5/2016 | Yasuno ............... A61B 3/0025 351/206 |

FOREIGN PATENT DOCUMENTS

| | | |
|---|---|---|
| JP | 2014-140490 A | 8/2014 |
| JP | 2015-513933 A | 5/2015 |

\* cited by examiner

SURGICAL SYSTEM, IMAGE PROCESSING DEVICE, AND IMAGE PROCESSING METHOD

TECHNICAL FIELD

The present technology relates to a surgical system, an image processing device, and an image processing method, and in particular to a surgical system, an image processing device, and an image processing method capable of obtaining the posture of an eye more firmly and with a high degree of accuracy.

BACKGROUND ART

Conventionally, a technology of presenting guide information as a guide for a surgeon when surgery is performed on an eye of a patient has been proposed (For example, refer to Patent Document 1). Specifically, the guide information such as a corneal range of the patient's eye and the orientation of an intraocular lens to be inserted into the eye is superimposed on an optical image or image of the intraoperative eye.

A possible method of presenting such guide information includes specifying the posture of the eye at each time during surgery, and a possible method of specifying the posture of the eye includes, for example, using a front image obtained by photographing the eye of the patient from the front.

Specifically, a possible method includes, for example, recognizing corneal and pupil ranges from preoperative and intraoperative front images, grasping a change from the preoperative position to the intraoperative position of the eye on the basis of the results of recognition, recognizing the correspondence relationship between the front images in terms of the blood vessels and iris, and thus detecting the turning angle around the eye axis of the eye as the posture of the eye. A possible method also includes presenting a wound creation position, an anterior capsule incision position, an intraocular lens orientation, and the like planned before surgery as the guide information on the basis of the turning angle or the like detected in this way.

CITATION LIST

Patent Document

Patent Document 1: Japanese Patent Application Laid-Open No. 2012-152469

SUMMARY OF THE INVENTION

Problems to be Solved by the Invention

However, with the above-described technology, it is difficult to obtain the posture of the eye firmly and with a high degree of accuracy, and the presented guide information may deviate greatly from the preoperative plan in some cases.

For example, in a case where a patient has the characteristics that make it difficult to observe the blood vessels from a front image, where the visibility of the blood vessels and iris is low due to photographing conditions for a front image, or where blown-out highlights occur in an image due to specular reflection of illumination or the like, it is difficult to estimate the turning angle of the eye from the front image. In addition, it is difficult to estimate the turning angle of the eye, for example, in a case where the eye of a patient is bleeding or where the contrast in a front image is low due to poor illumination.

Furthermore, although it is possible to estimate the three-dimensional posture of the eye from a front image, it is sometimes impossible to estimate the posture of the eye with a high degree of accuracy, resulting in the occurrence of a deviation from the presentation position of guide information.

The present technology has been made in view of such a situation, and an object thereof is to make it possible to obtain the posture of an eye more firmly and with a high degree of accuracy.

Solutions to Problems

A surgical system according to a first aspect of the present technology includes: a tomographic image acquisition unit configured to acquire a tomographic image that is a cross-sectional image taken in a direction substantially parallel to an eye axis direction of an eye that is a surgical target; an image recognition unit configured to recognize a predetermined part of the eye in the tomographic image on the basis of the tomographic image; and a posture calculation unit configured to calculate a posture of the eye on the basis of a result of recognition of the predetermined part.

The surgical system can further be provided with a front image acquisition unit configured to photograph the eye that is the surgical target substantially in the eye axis direction.

It is possible to cause the posture calculation unit to calculate the posture of the eye on the basis of the result of recognition of the predetermined part and a front image obtained by the front image acquisition unit.

According to the first aspect of the present technology, a tomographic image that is a cross-sectional image taken in a direction substantially parallel to an eye axis direction of an eye that is a surgical target is acquired, a predetermined part of the eye in the tomographic image is recognized on the basis of the tomographic image, and a posture of the eye is calculated on the basis of a result of recognition of the predetermined part.

An image processing device according to a second aspect of the present technology includes: an image recognition unit configured to recognize, on the basis of a tomographic image that is a cross-sectional image taken in a direction substantially parallel to an eye axis direction of an eye that is a surgical target, a predetermined part of the eye in the tomographic image; and a posture calculation unit configured to calculate a posture of the eye on the basis of a result of recognition of the predetermined part.

It is possible to cause the posture calculation unit to calculate, as the posture of the eye, a turning angle of the eye around the eye axis serving as a rotation axis.

It is possible to cause the posture calculation unit to calculate a three-dimensional posture of the eye.

It is possible to cause the posture calculation unit to calculate the three-dimensional posture of the eye on the basis of an amount of rotation of the eye.

It is possible to cause the posture calculation unit to calculate the posture of the eye on the basis of a positional relationship between an optic disc and a fovea recognized as the predetermined part.

It is possible to cause the image recognition unit to recognize the predetermined part of the eye on the basis of the tomographic image of the eye taken before or during surgery.

It is possible to cause the image recognition unit to recognize, on the basis of a front image obtained by photographing the eye substantially in the eye axis direction, a specific part of the eye in the front image, and to recognize the predetermined part in the tomographic image using, as a target, a region on the tomographic image designated by applying a result of recognition of the specific part.

It is possible to cause the posture calculation unit to calculate a final posture of the eye on the basis of a result of calculation of the posture of the eye that is based on the result of recognition of the predetermined part and on the basis of a front image obtained by photographing the eye substantially in the eye axis direction.

It is possible to cause the posture calculation unit to calculate the final posture of the eye on the basis of the front image within a range of posture designated by applying the result of calculation of the posture of the eye that is based on the result of recognition of the predetermined part.

It is possible to cause the image recognition unit to recognize, on the basis of a front image obtained by photographing the eye substantially in the eye axis direction, a specific part of the eye in the front image, and the image processing device can further be provided with an acquisition control unit configured to operate such that the tomographic image at a cross-sectional position designated by applying a result of recognition of the specific part is acquired.

It is possible to cause the image recognition unit to recognize, on the basis of a front image obtained by photographing the eye substantially in the eye axis direction during surgery on the eye, a surgical tool on the front image, and to recognize the predetermined part while excluding a region on the tomographic image designated by applying a result of recognition of the surgical tool.

It is possible to cause the image recognition unit to recognize the predetermined part in volume data obtained from a plurality of the tomographic images taken at different cross-sectional positions.

The image processing device can further be provided with a guide information generation unit configured to generate, on the basis of the posture of the eye, guide information as a guide for use in surgery on the eye.

The tomographic image can be an image photographed with an optical coherence tomography device.

An image processing method according to the second aspect of the present technology includes the steps of: recognizing, on the basis of a tomographic image that is a cross-sectional image taken in a direction substantially parallel to an eye axis direction of an eye that is a surgical target, a predetermined part of the eye in the tomographic image; and calculating a posture of the eye on the basis of a result of recognition of the predetermined part.

According to the second aspect of the present technology, on the basis of a tomographic image that is a cross-sectional image taken in a direction substantially parallel to an eye axis direction of an eye that is a surgical target, a predetermined part of the eye is recognized in the tomographic image, and a posture of the eye is calculated on the basis of a result of recognition of the predetermined part.

Effects of the Invention

According to the first and second aspects of the present technology, the posture of the eye can be obtained more firmly and with a high degree of accuracy.

Note that the effects described herein are not necessarily limited, and any of the effects described in the present disclosure may be obtained.

MODE FOR CARRYING OUT THE INVENTION

Hereinafter, embodiments to which the present technology is applied will be described with reference to the drawings.

First Embodiment

<Exemplary Configuration of Surgical System>

In the present technology, by using a tomographic image of an eye of a patient as a surgical target to recognize each part of the eye, it is possible to obtain the posture of the eye (eyeball) more firmly and with a high degree of accuracy.

Figure 1:
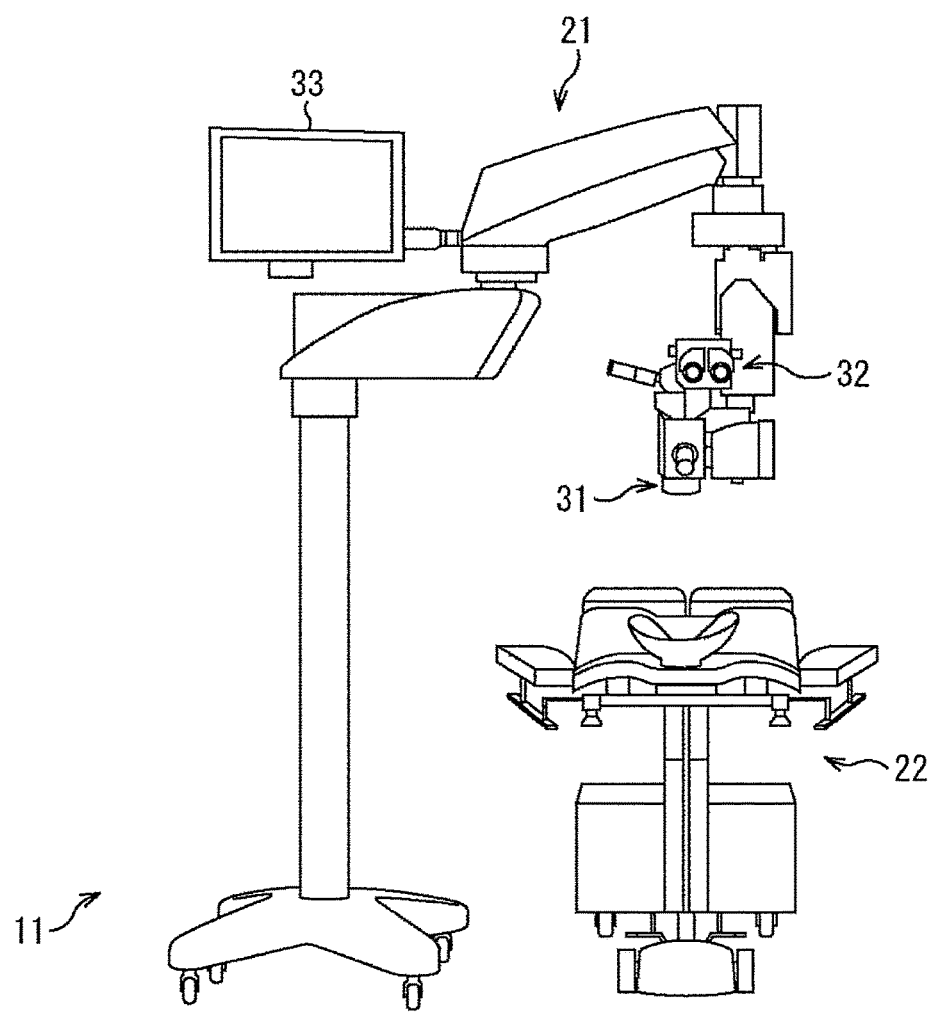
FIG. 1 is a view illustrating an exemplary configuration of a surgical system.

FIG. 1 is a view illustrating an exemplary configuration of an embodiment of a surgical system to which the present technology is applied.

The surgical system 11 illustrated in FIG. 1 has a surgical microscope 21 and a patient bed 22, and a patient undergoes surgery on the eye while lying on the patient bed 22. In addition, a doctor as a surgeon performs surgery while observing the eye of the patient using the surgical microscope 21.

Specifically, the surgical microscope 21 has an objective lens 31, an eyepiece 32, a monitor 33, and the like for magnifying and observing the eye of a patient as a surgical target. In this example, the doctor looks into the eyepiece 32 and performs surgery while observing the eye of the patient via the objective lens 31. In addition, a front image photographed with a camera (not illustrated) is displayed on the monitor 33.

At this time, if necessary, guide information is superimposed on an optical image of the eye of the patient observed through the eyepiece 32, or guide information is superimposed on the front image displayed on the monitor 33.

Figure 2:
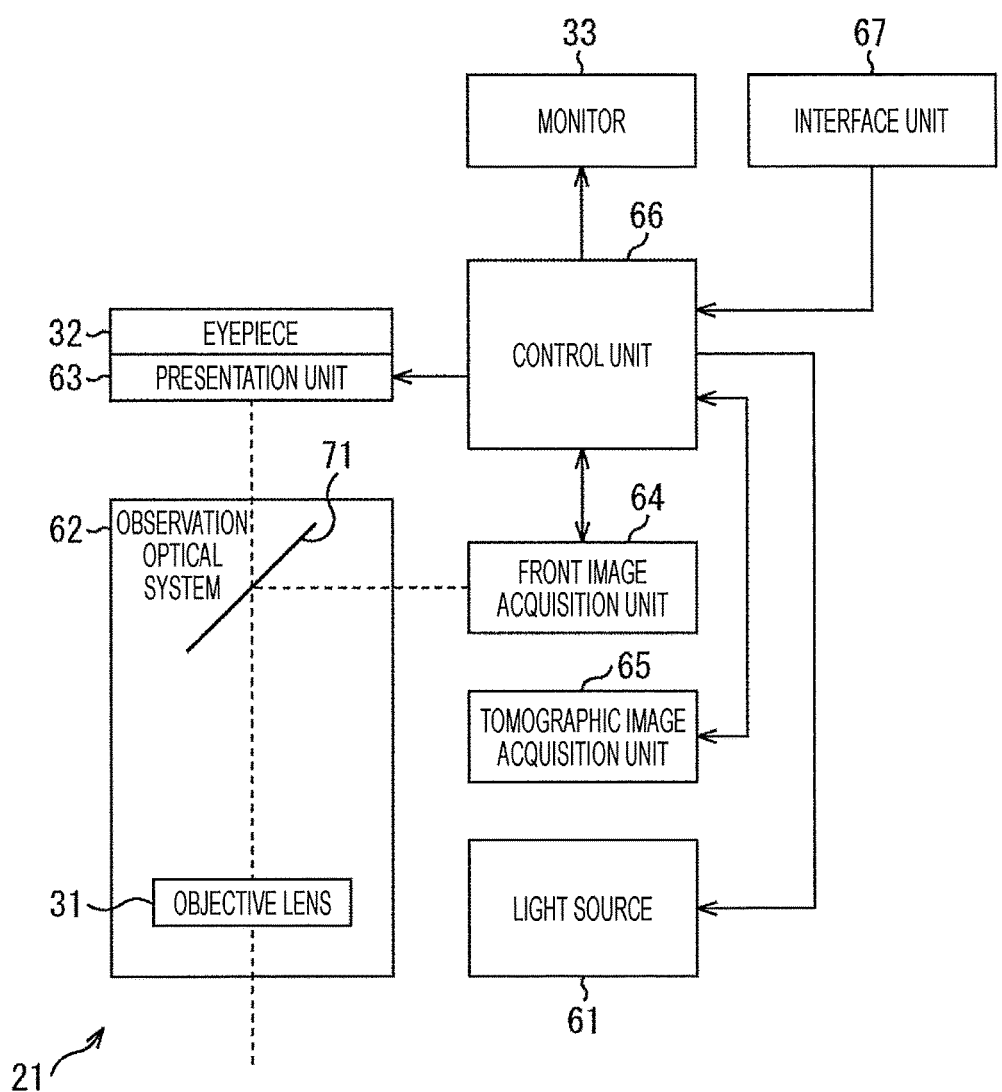
FIG. 2 is a diagram illustrating an exemplary configuration of a surgical microscope.

Further, the functional configuration of the surgical microscope 21 is as illustrated in FIG. 2, for example. Note that, in FIG. 2, a component corresponding to that in FIG. 1 is denoted by the same reference sign, and the description thereof is appropriately omitted.

The surgical microscope 21 illustrated in FIG. 2 has a light source 61, an observation optical system 62, a presentation unit 63, the eyepiece 32, a front image acquisition unit 64, a tomographic image acquisition unit 65, a control unit 66, an interface unit 67, and the monitor 33.

The light source 61 emits illumination light under the control of the control unit 66 to illuminate the eye of the patient. Further, the observation optical system 62 includes, for example, optical elements such as the objective lens 31, a 50/50 beam splitter 71, and a lens (not illustrated), and guides light (observation light) that has entered through the patient's eye to the eyepiece 32 and the front image acquisition unit 64.

Specifically, the observation light that has entered through the patient's eye enters the 50/50 beam splitter 71 through the objective lens 31, the lens (not illustrated), and the like. Almost half of the observation light that has entered the 50/50 beam splitter 71 passes through the 50/50 beam splitter 71 as it is and enters the eyepiece 32 via the transmissive presentation unit 63. On the other hand, the other half of the observation light that has entered the 50/50 beam splitter 71 is reflected by the 50/50 beam splitter 71 and enters the front image acquisition unit 64.

The eyepiece 32 converges the observation light that has entered through the observation optical system 62 via the presentation unit 63 and forms an optical image of the patient's eye. As a result, the surgeon looking into the eyepiece 32 observes the optical image of the patient's eye.

The front image acquisition unit 64 includes, for example, a video camera or the like. The front image acquisition unit 64 receives the observation light that has entered through the observation optical system 62, and photoelectrically converts the observation light, thereby taking an image of the patient's eye observed from the front, that is, a front image obtained by photographing the patient's eye substantially in the eye axis direction. The front image acquisition unit 64 photographs the front image under the control of the control unit 66 and supplies the obtained front image to the control unit 66.

The tomographic image acquisition unit 65 includes, for example, an optical coherence tomography (OCT) device, a Scheimpflug camera, or the like. The tomographic image acquisition unit 65 photographs a tomographic image which is a cross-sectional image of the eye of the patient under the control of the control unit 66 and supplies the obtained tomographic image to the control unit 66. As used herein, the tomographic image is a cross-sectional image taken in a direction substantially parallel to the eye axis direction of the eye of the patient.

Note that the tomographic image acquisition unit 65 acquires the tomographic image using, for example, infrared light on the basis of the interference principle. In this case, the optical path for infrared light and a part of the optical path for observation light within the observation optical system 62 may be a common optical path.

The control unit 66 controls the operation of the entire surgical microscope 21. The presentation unit 63 includes a transmissive display device and is disposed between the eyepiece 32 and the observation optical system 62. The presentation unit 63 allows the observation light that has entered through the observation optical system 62 to pass therethrough and enter the eyepiece 32, and presents (displays) the guide information supplied from the control unit 66. As a result, the guide information is superimposed on the optical image of the eye of the patient so as to be presented to the surgeon looking into the eyepiece 32.

The interface unit 67 includes, for example, a touch panel superimposed and provided on the monitor 33, a controller, a communication unit for receiving instructions from a remote controller (not illustrated) and communicating with external devices, and the like, and supplies information corresponding to the operation of the surgeon or the like to the control unit 66. In other words, the interface unit 67 acquires information and images corresponding to the operation and supplies them to the control unit 66.

The monitor 33 displays the front image under the control of the control unit 66. Further, in the monitor 33, the guide information may be superimposed on the front image.

For example, at the time of surgery on a patient, the control unit 66 first acquires, from the interface unit 67, preoperative planning information including information indicating the guide information to be presented as a guide, information indicating a presentation position of the guide information, and the like, and preoperative images which are front and tomographic images taken before the surgery.

Then, the control unit 66 controls the light source 61 to cause the light source 61 to emit illumination light. As a result, the eye of the patient is illuminated, and the surgeon can observe the eye of the patient through the eyepiece 32.

Further, the control unit 66 controls the front image acquisition unit 64 to cause the front image acquisition unit 64 to take a front image, supplies the obtained front image to the monitor 33, and causes the monitor 33 to display the front image. Furthermore, the control unit 66 controls the tomographic image acquisition unit 65 to cause the tomographic image acquisition unit 65 to photograph a tomographic image during the surgery as an intraoperative image, and estimates the posture of the eye from the obtained intraoperative image and the tomographic image as the preoperative image.

The control unit 66 generates guide information from the obtained posture of the eye and the preoperative planning information acquired in advance, and supplies the guide information to the presentation unit 63 and the monitor 33 for presentation (display). Thus, the surgeon can perform the surgery efficiently while referring to the guide information superimposed on the optical image of the eye of the patient as the surgical target. Further, in the monitor 33, the guide information is superimposed on the front image and displayed.

Note that, although the posture of the eye is obtained on the basis of the tomographic images in the example described above, the posture of the eye may be obtained using tomographic and front images.

<Regarding Guide Information>

Next, a specific example of the guide information will be described.

The present technology can be applied to, for example, surgery on a patient's eye. In the case of the following description, cataract surgery is performed on a patient as an example.

Figure 3:
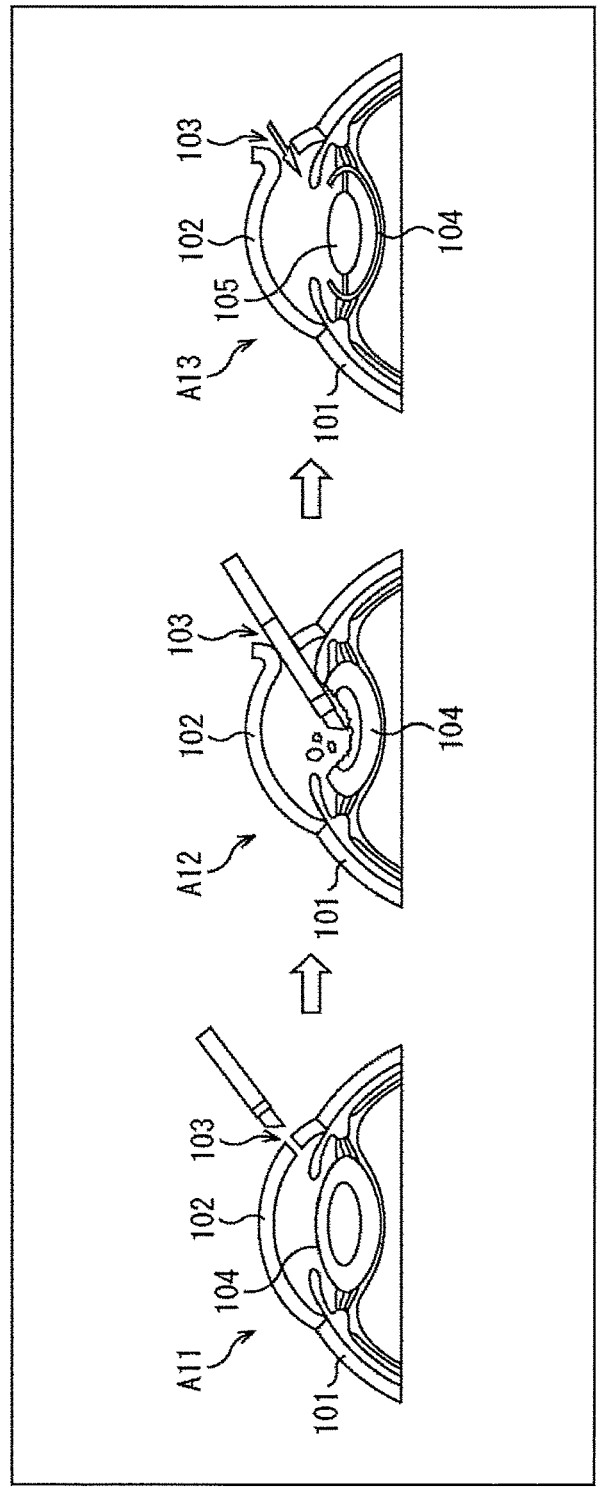
FIG. 3 is a diagram for explaining cataract surgery.

In cataract surgery, as illustrated by an arrow A11 in FIG. 3, a part of a cornea 102 of an eyeball 101 of the patient is first incised with a knife, and a wound 103 is created. Then, a surgical tool is inserted through the wound 103, and an anterior portion of a crystalline lens 104 located inside the eyeball 101, that is, an anterior capsule portion, is incised in a circular shape.

Then, as illustrated by an arrow A12, a surgical tool is inserted through the wound 103 into the anterior capsule incised portion of the crystalline lens 104. Emulsification (pulverization) and suction of the nucleus of the crystalline lens 104 are performed by means of ultrasonic vibration, which is called a nucleus treatment, and the cortex is also sucked. Thereafter, an intraocular lens 105 is inserted into the crystalline lens 104 as illustrated by an arrow A13, and the surgery is completed.

Figure 4:
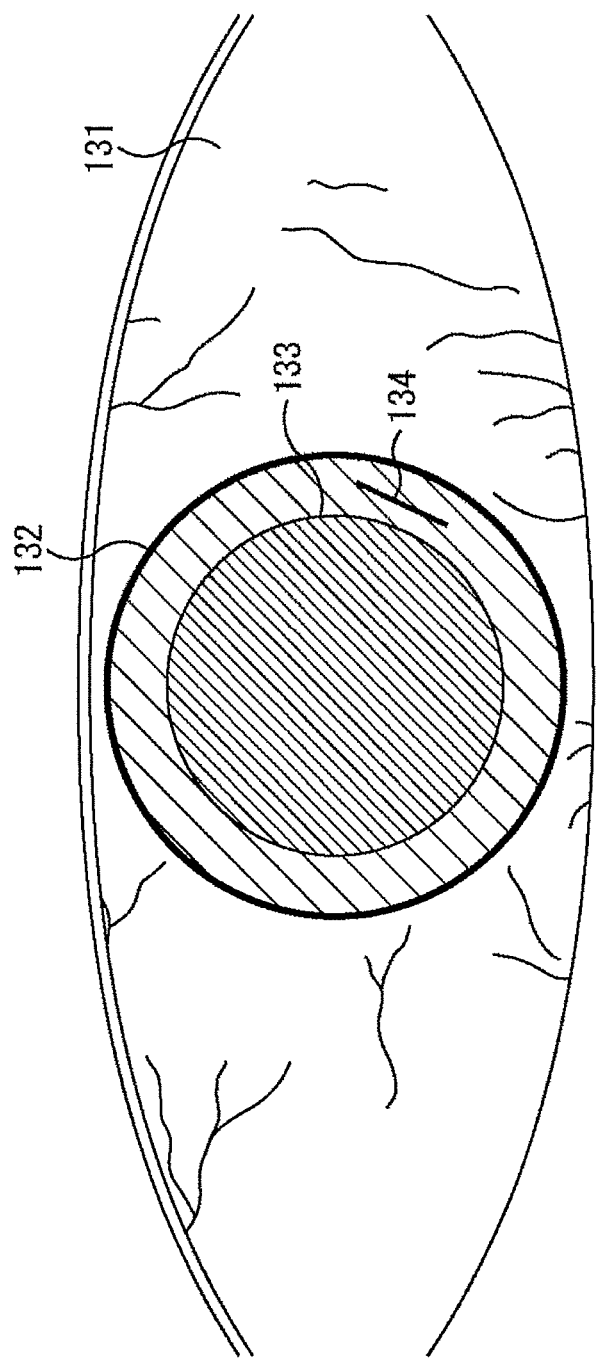
FIG. 4 is a diagram for explaining a preoperative plan.
Figure 5:
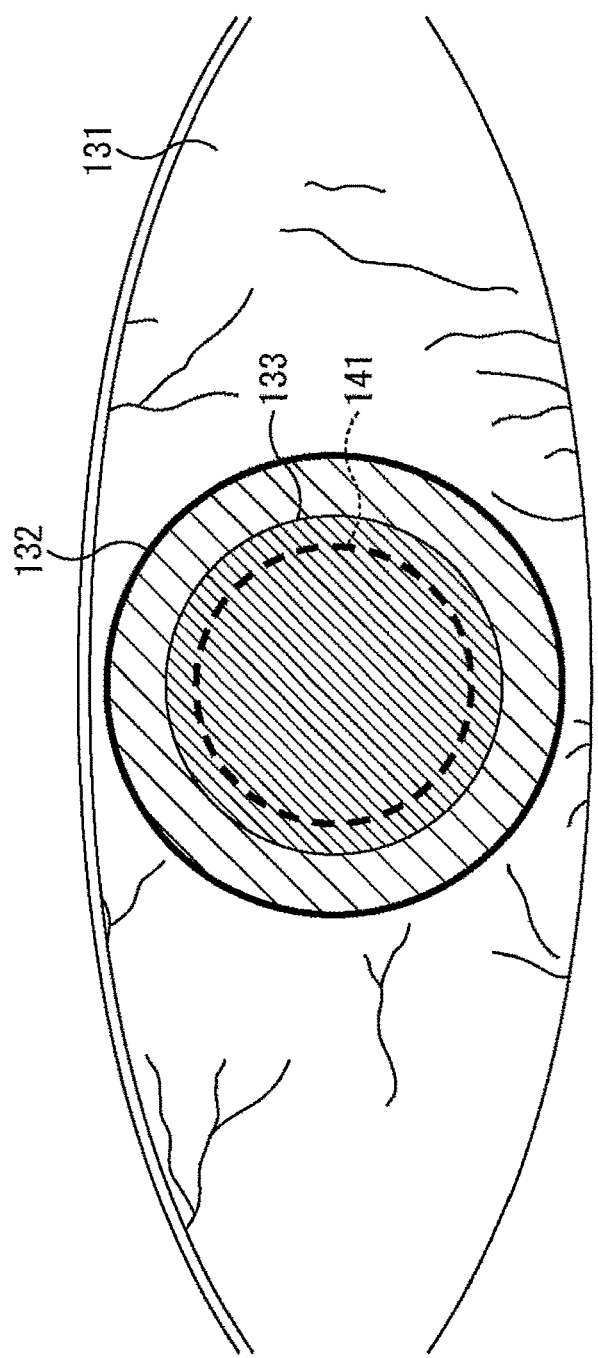
FIG. 5 is a diagram for explaining the preoperative plan.
Figure 6:
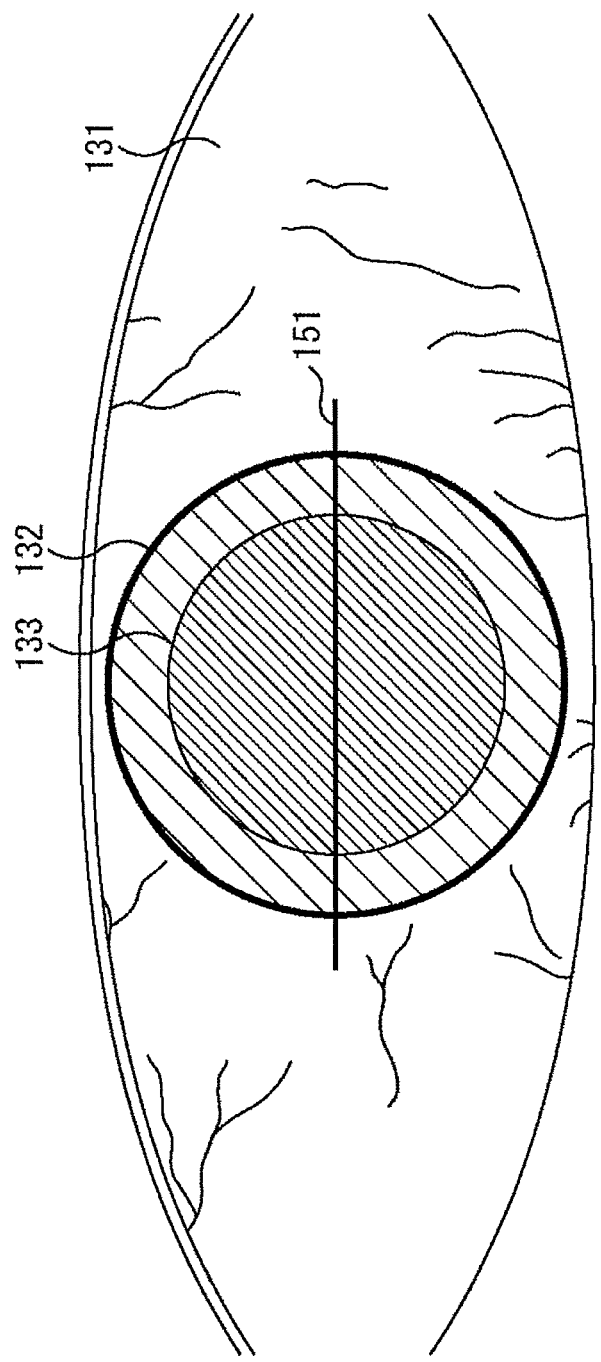
FIG. 6 is a diagram for explaining the preoperative plan.

In a case where the above-mentioned cataract surgery is performed, a preoperative plan illustrated in FIGS. 4 to 6 is established from a front image taken before the surgery. Note that, in FIGS. 4 to 6, components corresponding to one another are denoted by the same reference signs, and the description thereof is appropriately omitted.

First, in the preoperative plan, as illustrated in FIG. 4, for example, the position where a wound is to be created is designated at the cornea portion of an eye 131 of a patient on the front image, specifically in the vicinity of and inside a corneal limbus 132. In this example, the lower right part on the outside of a pupil 133 in the drawing is set as a wound creation position 134.

Subsequently, for example, as illustrated in FIG. 5, a circular region on the inside of the corneal limbus 132 in the eye 131 of the patient on the front image is designated as an anterior capsule incision position 141. For example, the radius of the circle illustrated as the anterior capsule incision position 141 is determined on the basis of the size of the intraocular lens and the like.

Further, as illustrated in FIG. 6, the direction of the intraocular lens with respect to the eye 131 of the patient on the front image for disposing the intraocular lens is designated as an intraocular lens orientation 151. In this example, the intraocular lens orientation 151 is represented by a straight line.

For example, the intraocular lens orientation 151 is designated on the basis of various kinds of information such as refraction information of each part of the eye including corneal refraction of the patient's eye and the wound creation position.

Figure 7:
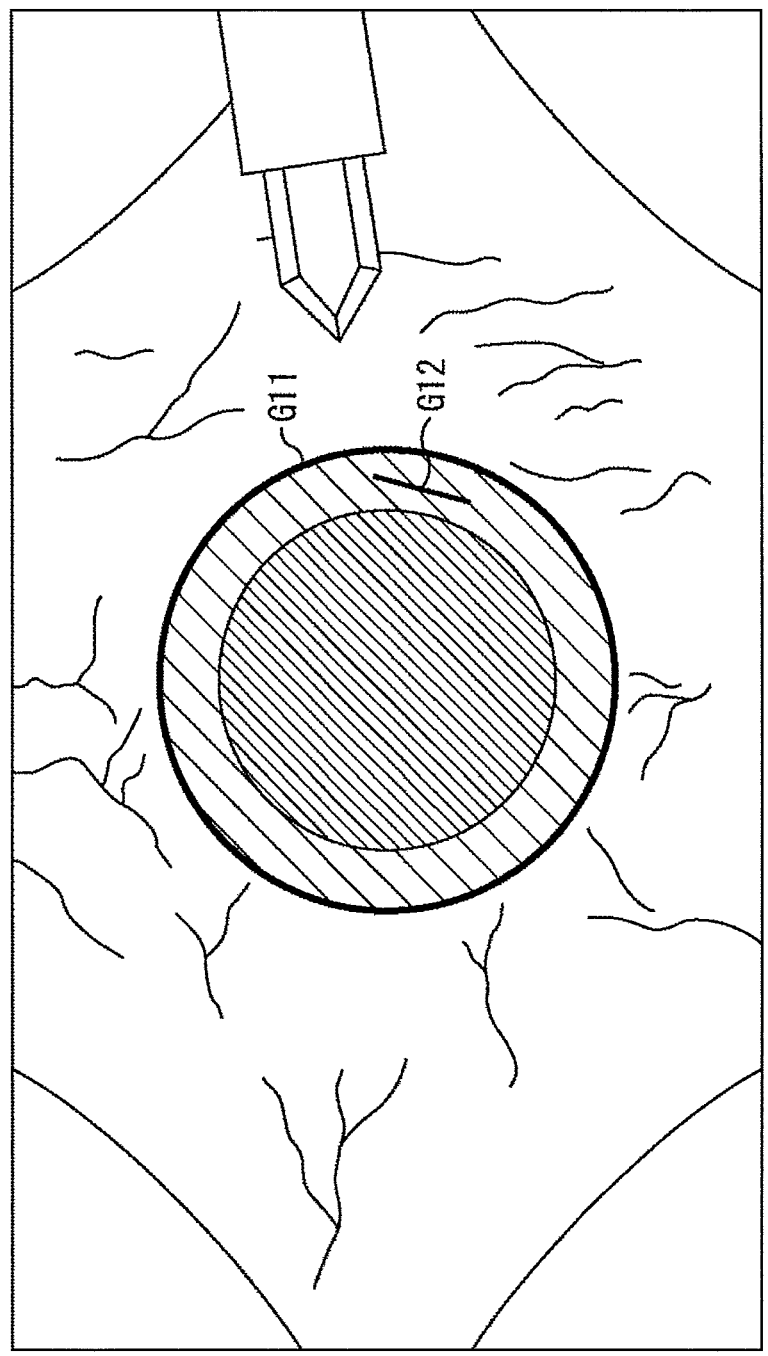
FIG. 7 is a diagram for explaining the presentation of guide information.
Figure 8:
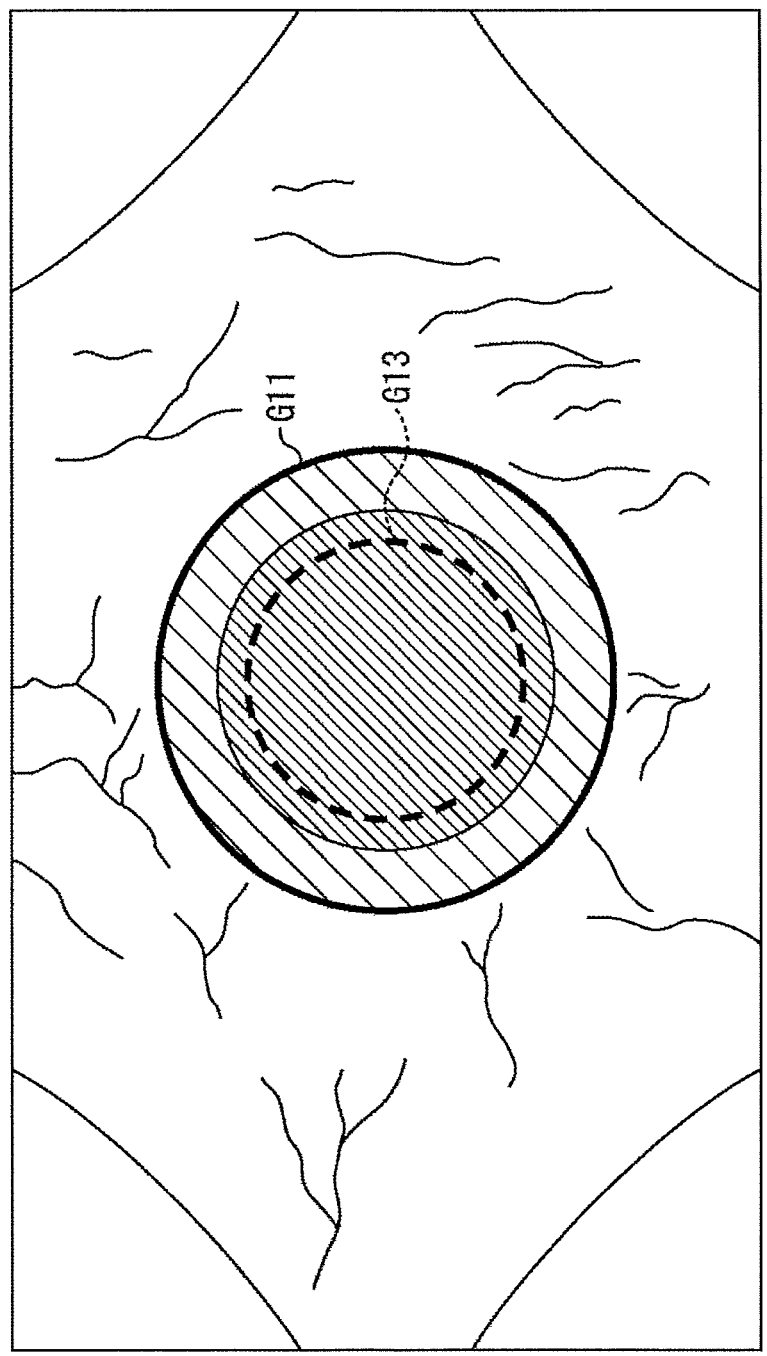
FIG. 8 is a diagram for explaining the presentation of the guide information.
Figure 9:
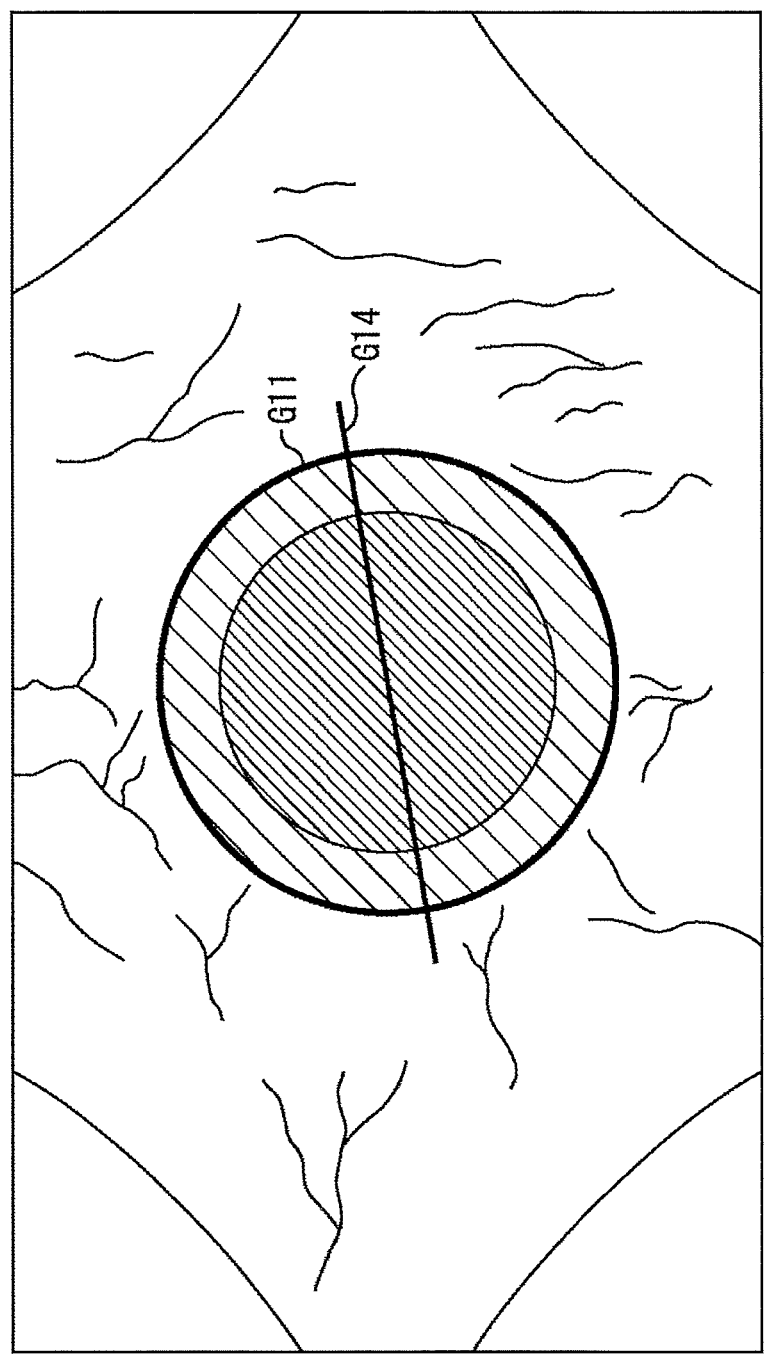
FIG. 9 is a diagram for explaining the presentation of the guide information.

After the wound creation position, the anterior capsule incision position, and the intraocular lens orientation are determined in the preoperative plan in this manner, guide information is presented during surgery according to the preoperative plan as illustrated, for example, in FIGS. 7 to 9. Note that, in FIGS. 7 to 9, components corresponding to one another are denoted by the same reference signs, and the description thereof is appropriately omitted.

At the time of cataract surgery, when the surgeon looks into the eyepiece 32, an optical image of the eye of the patient is observed as illustrated in FIG. 7. Then, corneal limbus information G11 indicating the corneal limbus, that is, the boundary between the cornea and the sclera, and wound position information G12 indicating the wound creation position are superimposed on the optical image of the eye of the patient and presented (displayed) on the presentation unit 63 as the guide information. The surgeon incises the part on which the wound position information G12 is displayed with a knife to create a wound.

At this time, the corneal limbus information G11 and the wound position information G12 that are presented as the guide information correspond to the corneal limbus 132 and the wound creation position 134 illustrated in FIG. 4, and are presented at the same positions as the corneal limbus 132 and the wound creation position 134, respectively. Specifically, the presentation position of the guide information is adjusted according to the movement of the eye so that the guide information is always presented at a specific part on the optical image of the eye of the patient.

As the surgery further proceeds, the corneal limbus information G11 and anterior capsule incision position information G13 indicating the incision position of the anterior capsule are superimposed on the optical image of the eye of the patient as illustrated in FIG. 8 and presented on the presentation unit 63 as the guide information. The surgeon incises the part on which the anterior capsule incision position information G13 is displayed in the eye of the patient.

In the example of FIG. 8 as well as in FIG. 7, the corneal limbus information G11 and the anterior capsule incision position information G13 that are presented as the guide information are displayed at the positions corresponding to the corneal limbus 132 and the anterior capsule incision position 141 illustrated in FIG. 5, respectively.

After the anterior capsule is incised and the nuclear treatment and the sebum suction are performed, as illustrated in FIG. 9, the corneal limbus information G11 and intraocular lens direction information G14 indicating the orientation of the intraocular lens are superimposed on the optical image of the eye of the patient and presented on the presentation unit 63 as the guide information. The surgeon inserts the intraocular lens into the crystalline lens of the patient's eye such that the intraocular lens is oriented in the direction indicated by the intraocular lens direction information G14.

In FIG. 9, the corneal limbus information G11 and the intraocular lens direction information G14 that are presented as the guide information are displayed at the positions corresponding to the corneal limbus 132 and the intraocular lens orientation 151 illustrated in FIG. 6, respectively.

As described above, in a case where cataract surgery is performed, for example, the corneal limbus information G11, the wound position information G12, the anterior capsule incision position information G13, and the intraocular lens direction information G14 are presented as the guide information. When presenting these pieces of guide information, it is important to estimate the position of each part of the eye of the patient and the posture of the eye during surgery firmly and with a high degree of accuracy in order to prevent a deviation between the presentation position of the guide information prescribed in the preoperative plan and the actual intraoperative presentation position of the guide information.

In a case where the parts and posture of the eye are estimated using a front image as described above, the estimation accuracy may be lowered, or it may be difficult to perform the estimation in the first place depending on the situation. Therefore, in the present technology, by using a tomographic image of the eye of the patient, each part of the eye of the patient and the posture of the eye can be estimated more firmly and with a high degree of accuracy.

For example, if a tomographic image is acquired (photographed) by the tomographic image acquisition unit 65 including an optical coherence tomography device or the like, it is possible to recognize (detect) parts such as the boundary position between the cornea and the sclera, the corner angle, and the end point (inner edge) of the iris more firmly from the tomographic image, irrespective of photographing conditions such as illumination, personal characteristics that make it difficult to observe the blood vessels, and the like. In addition, in this case, the influence of intraoperative bleeding on the recognition of each part of the eye is sufficiently small, as compared with the case of using a front image.

If each part of the eye can be recognized more firmly and with a high degree of accuracy using the tomographic image in this manner, the posture of the patient's eye can be estimated more firmly and with a high degree of accuracy using the result of recognition. In addition, it is possible to present guide information with a higher degree of accuracy by using the result of recognition of each part of the patient's eye and the result of estimation of the posture of the patient's eye.

Figure 10:
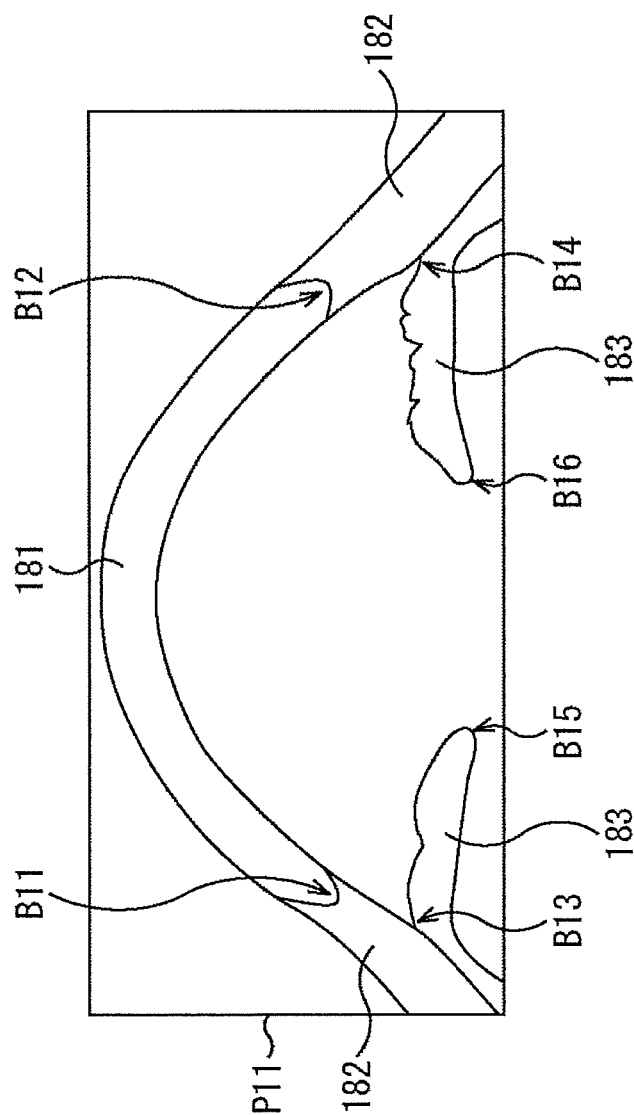
FIG. 10 is a diagram for explaining a tomographic image.

For example, in the tomographic image acquisition unit 65, a tomographic image P11 illustrated in FIG. 10 can be obtained. Note that, to be more specific, the tomographic image P11 illustrates only a part of the tomographic image actually obtained.

The tomographic image P11 illustrated in FIG. 10 is a cross-sectional image substantially parallel to the eye axis of a patient's eye and substantially perpendicular to a front image. In this tomographic image P11, a cornea 181, a sclera 182, and an iris 183 of the patient's eye are observed.

In the control unit 66 of the surgical microscope 21, each part of the eye can be recognized from the tomographic image P11 by means of image recognition with a dictionary learned in advance or image recognition that utilizes image contrast. For example, a boundary position B11 and a boundary position B12 which are the boundary portions between the cornea 181 and the sclera 182, an angle position B13 and an angle position B14 which are the positions of the angles formed by the sclera 182 and the iris 183, an iris end point B15 and an iris end point B16 which are the end points (inner edges) of the iris, and the like can be recognized by means of image recognition. Furthermore, from the tomographic image, the position of the optic disc and the position of the fovea in the posterior segment of the eye can also be obtained by means of image recognition.

Figure 11:
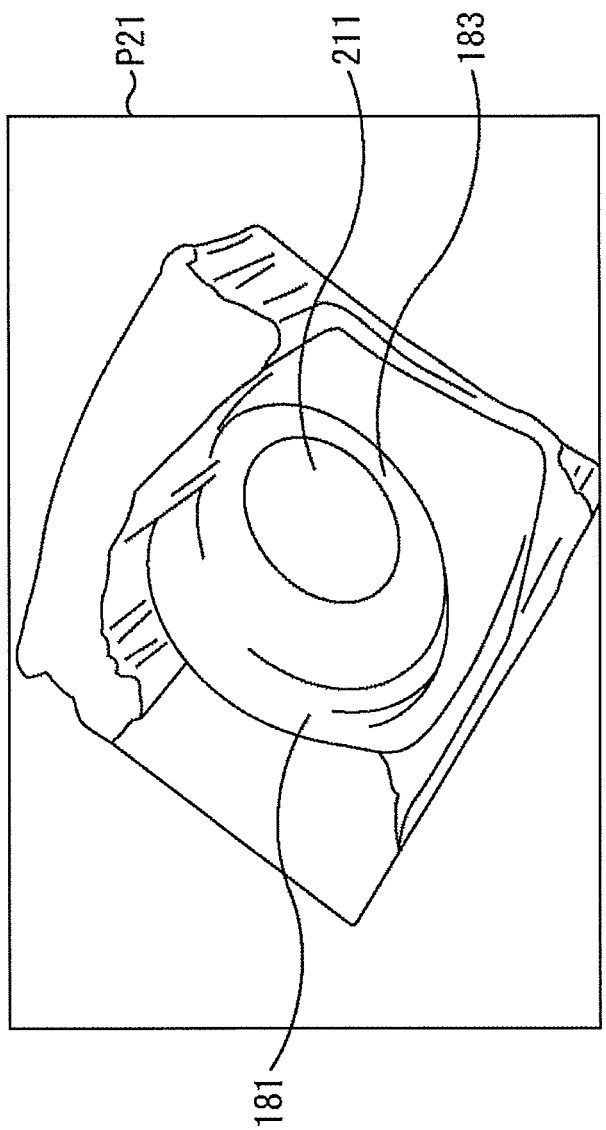
FIG. 11 is a diagram for explaining volume data of tomographic images.

In addition, in the control unit 66, volume data P21 illustrated, for example, in FIG. 11 can be obtained from tomographic images obtained at respective cross-sectional positions by the tomographic image acquisition unit 65. Note that, in FIG. 11, a component corresponding to that in FIG. 10 is denoted by the same reference sign, and the description thereof is appropriately omitted.

The volume data P21 is a stereoscopic image indicating the three-dimensional shape of the eye of the patient, i.e., a subject of tomographic images, reconstructed from a plurality of tomographic images taken at different cross-sectional positions. Specifically, the volume data P21 is an image obtained as the result of accumulation of the tomographic images taken at the respective cross-sectional positions.

For example, in the volume data P21, the cornea 181, the iris 183, and a pupil 211 of the patient's eye are observed, and the corneal limbus that is the boundary of the cornea 181 and the outline of the pupil 211 that is the boundary portion between the iris 183 and the pupil 211 can be obtained directly from the volume data P21.

Further, in the control unit 66, an image of the eye of the patient viewed in the direction identical to the photographing direction of the front image obtained by the front image acquisition unit 64, that is, the eye axis direction, can be obtained by reconstructing the subject using the tomographic images obtained at the respective cross-sectional positions by the tomographic image acquisition unit 65.

Hereinafter, the image of the eye of the patient, reconstructed from the tomographic images, viewed in the direction identical to the photographing direction of the front image is also referred to as a reconstructed front image. In the following description, the photographing direction of the front image is also referred to as a front direction.

The control unit 66 recognizes a corneal range, a pupil range, and the posture of the eye (eyeball) which are necessary for presenting the guide information by appropriately using the tomographic image, the volume data, and the reconstructed front image described above. Note that the pupil range is not necessarily required, and is obtained only in a case where it is used to determine the presentation position of the guide information.

Hereinafter, the recognition of the corneal range, the pupil range, and the posture of the eye will be described.

(Regarding Recognition of Corneal Range)

For example, the corneal range can be obtained by recognizing the angle positions or boundary positions between the cornea and the sclera as indicated in (A) and (B) below.

(A) Obtain the corneal range from the angle positions (1) Estimate the corneal range from the angle positions in one or several tomographic images (2) Set the inside of the angle in the volume data of tomographic images as the corneal range (B) Obtain the corneal range from the boundary positions between the cornea and the sclera (1) Estimate the corneal range from the boundaries between the cornea and the sclera in one or several tomographic images (2) Set the inside of the boundary between the cornea and the sclera in the volume data of tomographic images as the corneal range Specifically, in a case where the corneal range is obtained using the method indicated in (1) of (A), two angle positions are recognized by means of image recognition from each of one or several tomographic images. For example, in the example illustrated in FIG. 10, the angle position B13 and the angle position B14 are recognized from the tomographic image P11.

Then, the corneal range is estimated on the basis of the respective angle positions on the tomographic images recognized in this manner and the cross-sectional positions of the respective tomographic images.

Specifically, for example, in a case where a plurality of tomographic images is used, the positions, viewed in the front direction, of the angle positions recognized in each tomographic image are obtained, and the region inside the circle (annular line) obtained by connecting the angle positions adjacent to each other when viewed in the front direction is regarded as the corneal range. Upon generation of the guide information, the outline portion of the corneal range obtained in this manner is regarded as the corneal limbus.

In addition, in a case where the corneal range is obtained using the method indicated in (2) of (A), the angle position is recognized by means of image recognition from the volume data of tomographic images. In this case, since the three-dimensional shape of the corner angle is obtained as the result of recognition, the region inside the annular (circular) angle portion obtained as the result of recognition is regarded as the corneal range.

In a case where the corneal range is obtained using the method indicated in (1) of (B), two boundary positions between the cornea and the sclera are recognized by means of image recognition from each of one or several tomographic images. For example, in the example illustrated in FIG. 10, the boundary position B11 and the boundary position B12 are recognized from the tomographic image P11.

Then, the corneal range is estimated on the basis of the respective boundary positions on the tomographic images recognized in this manner and the cross-sectional positions of the respective tomographic images in a manner similar to the method indicated in (1) of (A). Specifically, for example, the region inside the circle obtained by connecting the boundary positions between the cornea and the sclera adjacent to each other when viewed in the front direction is regarded as the corneal range.

Furthermore, in a case where the corneal range is obtained using the method indicated in (2) of (B), the boundary position between the cornea and the sclera is recognized by means of image recognition from the volume data of tomographic images. In this case, the three-dimensional shapes of the cornea and sclera are obtained as the result of recognition. Therefore, since the boundary between the cornea and the sclera obtained as the result of recognition has an annular (circular) shape, the region inside the annular boundary is regarded as the corneal range.

(Regarding Recognition of Pupil Range)

Moreover, for example, the pupil range can be obtained on the basis of the positions of the end points of the iris as indicated in (1) or (2) of (C) below.

(C) Find the pupil range from the end point positions of the iris (1) Estimate the pupil range from the end point positions of the iris in one or several tomographic images (2) Set the inside of the iris end point in the volume data of tomographic images as the pupil range Specifically, in a case where the pupil range is obtained using the method indicated in (1) of (C), two end point positions of the iris are recognized by means of image recognition from each of one or several tomographic images. For example, in the example illustrated in FIG. 10, the iris end point B15 and the iris end point B16 are recognized from the tomographic image P11.

Then, the pupil range is estimated on the basis of the respective iris end points on the tomographic images recognized in this manner and the cross-sectional positions of the respective tomographic images.

Specifically, for example, in a case where a plurality of tomographic images is used, the positions, viewed in the front direction, of the iris end point positions recognized in each tomographic image are obtained, and the region inside the circle obtained by connecting the iris end point positions adjacent to each other when viewed in the front direction is regarded as the pupil range. Upon generation of the guide information, the presentation position of the guide information is determined by appropriately utilizing the pupil range obtained in this manner.

In addition, in a case where the pupil range is obtained using the method indicated in (2) of (C), the iris is recognized by means of image recognition from the volume data of tomographic images. In this case, since the three-dimensional shape of the iris is obtained as the result of recognition, the region located further inside the inner end point of the iris obtained as the result of recognition, that is, the region having an annular (circular) shape and located further inside the inner end portion of the iris, is regarded as the pupil range.

(Regarding Recognition of Posture of Eye)

Furthermore, as the posture of the eye (eyeball), for example, the turning angle of the eye viewed in the front direction, that is, the rotation angle of the eyeball around the eye axis serving as the rotation axis, and the three-dimensional posture of the eyeball are considered.

As used herein, the turning angle of the eye is the rotation angle of the eyeball obtained in an intraoperative image with reference to a preoperative image when the eye is viewed in the front direction, that is, the change amount of the eyeball position around the eye axis.

For example, in a case where the turning angle is obtained as the posture of the eye, the turning angle of the eye can be obtained from the positional relationship between the optic disc and the fovea or from the distribution of the blood vessels as indicated in (1) to (3) of (D) below.

(D) Obtain the turning angle of the eyeball as the posture of the eye (1) Obtain from the positional relationship between the optic disc and the fovea in the volume data of tomographic images (2) Obtain from the positional relationship between depressions in the optic disc and in the fovea in several tomographic images (3) Obtain from the distribution of the blood vessels in several tomographic images or in the volume data of tomographic images Specifically, according to the method indicated in (1) of (D), the depression in the optic disc portion and the depression in the fovea portion are obtained by means of image recognition from the volume data of tomographic images, and the line segment connecting the depression in the optic disc portion and the depression in the fovea portion is obtained as a turning angle detection line. Then, the angle viewed in the front direction and formed by a preoperative turning angle detection line and an intraoperative turning angle detection line is obtained as the turning angle of the eyeball.

According to the method indicated in (2) of (D), the depression in the optic disc portion and the depression in the fovea portion are obtained by means of image recognition from each of a plurality of tomographic images. Then, on the basis of the result of recognition, e.g., the depth of the depression and the cross-sectional position of each tomographic image, the positions of the optic disc and fovea viewed in the front direction are estimated, and the turning angle detection line is obtained from the positional relationship between the optic disc and the fovea, whereby the turning angle of the eyeball is obtained.

In addition, according to the method indicated in (3) of (D), the distribution of the blood vessels is obtained by means of image recognition from several tomographic images or from the volume data of tomographic images, and the preoperative distribution of the blood vessels is compared (matched) with the intraoperative distribution of the blood vessels, whereby the turning angle of the eyeball is obtained.

Further, for example, in a case where the three-dimensional posture of the eyeball, that is, the posture of the eyeball in three-dimensional space, is obtained as the posture of the eye, the posture of the eye can be obtained by obtaining a change in the position of each part of the eye as indicated in (1) or (2) of (E) below.

(E) Obtain the three-dimensional posture of the eyeball as the posture of the eye (1) Obtain by combining a part or all of (A) to (D) above (2) Obtain by combining a combination of a part or all of (A) to (D) above and the three-dimensional shape of a part of the eye According to the method indicated in (1) of (E), for example, the corneal range is recognized using the method indicated in (A) or (B), the pupil range is recognized using the method indicated in (C), and the positional relationship (turning angle detection line) between the optic disc and the fovea is recognized using the method indicated in (D).

Then, the positional relationship of the eyeball in three-dimensional space is obtained as the three-dimensional posture of the eyeball from the corneal range, the pupil range, and the positional relationship between the preoperative and intraoperative turning angle detection lines.

Here, the three-dimensional posture of the eyeball can be obtained, for example, on the basis of the amount of rotational movement of the eye in three-dimensional space. Specifically, the three-dimensional posture of the eyeball can be expressed, for example, by a matrix indicating the amount of movement (amount of rotation) obtained when the preoperative position of a predetermined part of the eye, that is, coordinates (x, y, z) in a three-dimensional coordinate system, moves to coordinates (x', y', z') during surgery. To be specific, as indicated in Formula (1) below, the three-dimensional posture of the eyeball can be expressed by a transformation matrix for transforming the coordinates (x, y, z) to the coordinates (x', y', z').

[Mathematical Formula 1]

$$\begin{pmatrix} x' \\ y' \\ z' \end{pmatrix} = \begin{pmatrix} a_{11} & a_{12} & a_{13} \\ a_{21} & a_{22} & a_{23} \\ a_{31} & a_{32} & a_{33} \end{pmatrix} \begin{pmatrix} x \\ y \\ z \end{pmatrix} \quad (1)$$

In Formula (1), each element $a_{ij}$ (i=1, 2, 3, j=1, 2, 3) of the transformation matrix only needs to be defined such that the norm of the vector of each row of the transformation matrix is one, or such that the vectors of the respective rows are orthogonal to one another, for example.

In addition, in a case where the transformation matrix indicated in Formula (1) is regarded as information indicating the three-dimensional posture of the eyeball, parallel movement of the eyeball is ignored, and only the orientation of the eyeball, that is, rotational movement, is taken into consideration.

Furthermore, according to the method indicated in (2) of (E), in addition to the method indicated in (1) of (E) above, the three-dimensional shapes of the sclera, retina, and the like obtained from the volume data of tomographic images are also taken into consideration for obtaining the transformation matrix, and the transformation matrix is regarded as the three-dimensional posture of the eyeball.

Note that the corneal range, the pupil range, and the posture of the eye to be obtained from the tomographic images or volume data using the methods indicated in (A) to (E) described above may be obtained not only from tomographic images photographed during surgery but also from tomographic images photographed before surgery. In this case, for example, each part of the preoperative eye and the posture of the preoperative eye for use as a reference are obtained on the basis of tomographic images photographed before surgery, and a preoperative plan is established.

Once the corneal range, the pupil range, and the posture of the eye are obtained in the above-mentioned manner, guide information can be superimposed and presented on optical and front images of the intraoperative eye using the corneal range, the pupil range, and the posture of the eye.

At this time, in order to present the guide information, it is necessary to obtain in advance the positional relationship between the parts of the eye such as the corneal range and the pupil range and the guide information to be presented as a guide.

Figure 12:
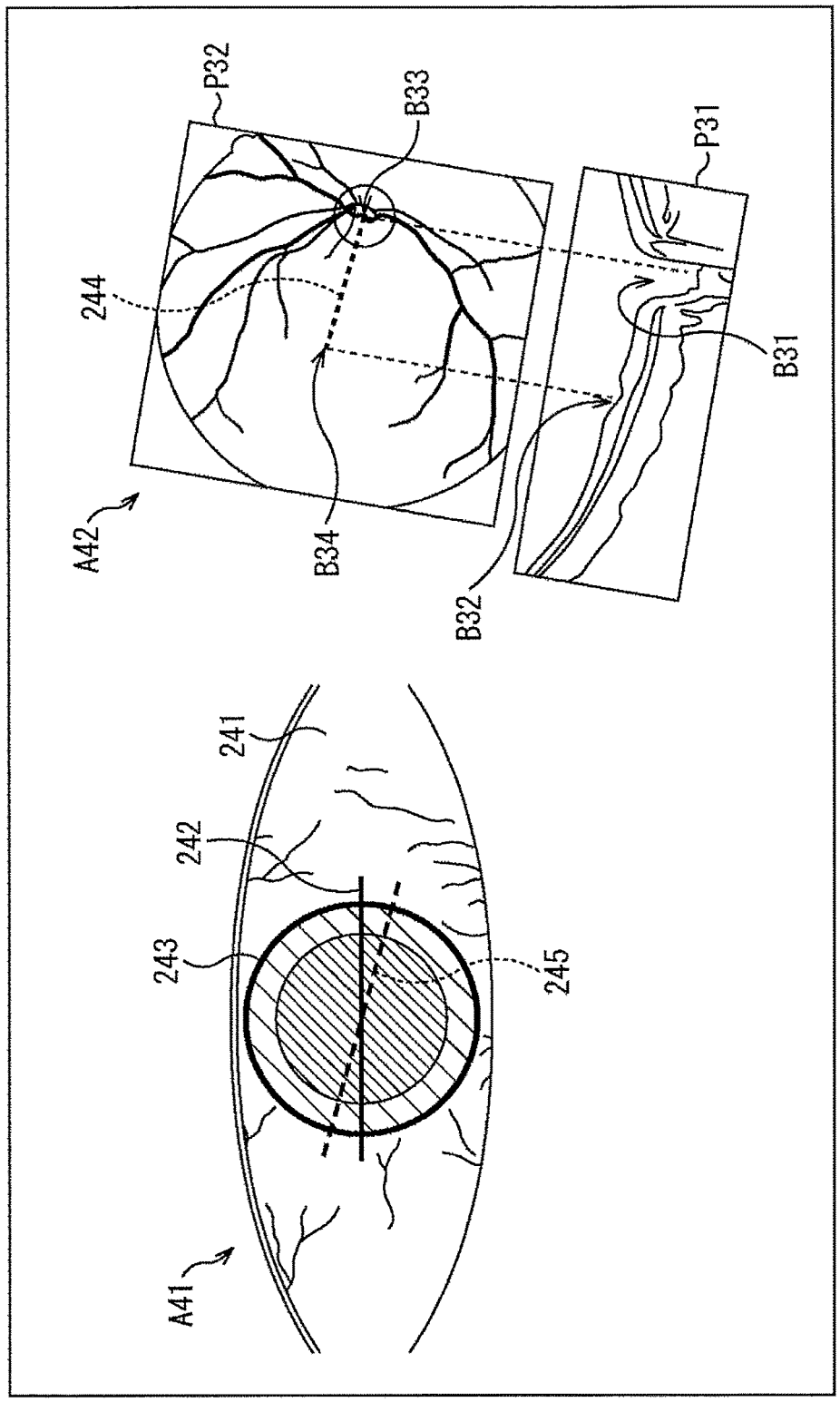
FIG. 12 is a diagram for explaining a preoperative plan.

For example, in a case where the intraocular lens direction information is presented as the guide information, as illustrated in FIG. 12, an angle θ formed by the direction of an intraocular lens indicated by the intraocular lens direction information and a turning angle detection line is obtained in advance at the time of preoperative planning.

Specifically, as illustrated by an arrow A41 in FIG. 12, it is assumed that the direction of the intraocular lens with respect to an eye 241 of a patient in a front image photographed by the front image acquisition unit 64 before surgery is designated as an intraocular lens orientation 242. In this example, during surgery, corneal limbus information corresponding to a corneal limbus 243 in the eye 241 of the patient and intraocular lens direction information corresponding to the intraocular lens orientation 242 are presented as the guide information.

In this case, as illustrated by an arrow A42, on the basis of several tomographic images including a tomographic image P31 acquired by the tomographic image acquisition unit 65 before surgery and the volume data of tomographic images, the positions of the optic disc and fovea are obtained by means of image recognition in a manner similar to the method indicated in (1) of (D) or (2) of (D) mentioned above.

In this example, a depression in the portion illustrated by an arrow B31 in the tomographic image P31 is recognized as the optic disc portion, and a depression in the portion illustrated by an arrow B32 is recognized as the fovea portion.

From such results of recognition, the positional relationship between the optic disc and the fovea in a reconstructed front image P32 reconstructed, for example, from the tomographic image P31 and the like is obtained. In this example, the portion illustrated by an arrow B33 in the reconstructed front image P32 indicates the optic disc portion, and the portion illustrated by an arrow B34 indicates the fovea portion. Then, the line segment (straight line) connecting the optic disc and the fovea is obtained as a turning angle detection line 244.

Once the turning angle detection line 244 is obtained in the front direction in this manner, the direction of the turning angle detection line in the front image illustrated by the arrow A41 is also obtained. In the drawing illustrated by the arrow A41, a straight line 245 indicates the direction of the turning angle detection line.

In the preoperative plan, for example, the angle formed by the direction of the turning angle detection line indicated by the straight line 245 and the direction indicated by the intraocular lens orientation 242 is obtained as the angle θ and regarded as a piece of preoperative planning information indicating the preoperative plan.

Figure 13:
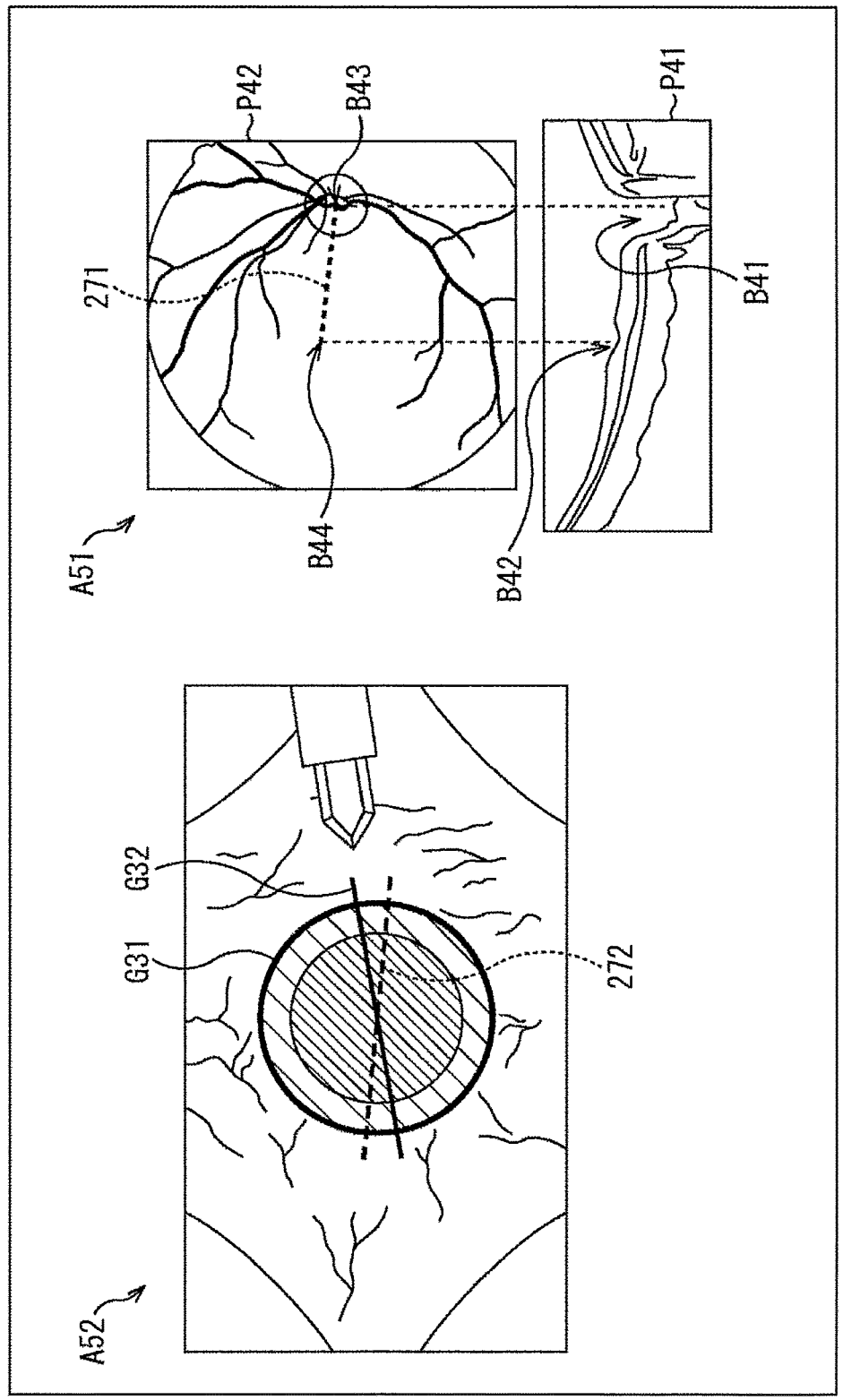
FIG. 13 is a diagram for explaining the presentation of guide information.

In addition, at the time of surgery, as illustrated by an arrow A51 in FIG. 13, on the basis of several tomographic images including a tomographic image P41 acquired by the tomographic image acquisition unit 65 during surgery and the volume data of the tomographic images, the turning angle is obtained as the posture of the eye in a manner similar to the method indicated in (1) of (D) or (2) of (D) mentioned above.

Specifically, the positions of the optic disc and fovea are obtained first by means of image recognition. In this example, a depression in the portion illustrated by an arrow B41 in the tomographic image P41 is recognized as the optic disc portion, and a depression in the portion illustrated by an arrow B42 is recognized as the fovea portion.

Then, from the results of recognition of the optic disc and fovea, the positional relationship between the optic disc and the fovea in a reconstructed front image P42 reconstructed, for example, from the tomographic image P41 and the like is obtained. In this example, the portion illustrated by an arrow B43 in the reconstructed front image P42 indicates the optic disc portion, and the portion illustrated by an arrow B44 indicates the fovea portion.

Note that, in the example used in the above description, the tomographic image P31 and the tomographic image P41 are acquired precisely along the optic disc and the fovea. However, even in a case where the tomographic image including both the optic disc and the fovea cannot be acquired, it is possible to estimate the positions of the optic disc and fovea on the basis of the position of a depression in the volume data including a plurality of tomographic images or on the basis of the position and dimensions of a depression in each of a plurality of tomographic images.

Once the positional relationship between the optic disc and the fovea viewed in the frontal direction is thus obtained, the line segment (straight line) connecting the optic disc and the fovea is obtained as a turning angle detection line 271, and the turning angle of the eyeball is obtained from the turning angle detection line 271 and the preoperative turning angle detection line.

Then, the angle at which the intraocular lens direction information as the guide information is presented can be found from the turning angle of the eyeball. Therefore, corneal limbus information G31 and intraocular lens direction information G32 are superimposed on the optical image of the eye of the patient and presented as the guide information as illustrated by an arrow A52.

Here, the corneal limbus information G31 is specified by the corneal range obtained by means of image recognition during surgery. Further, the presentation direction of the intraocular lens direction information G32 is obtained from the turning angle of the eyeball. Specifically, the intraocular lens direction information is presented in such a state that it is rotated by the obtained turning angle with respect to the presentation direction of the intraocular lens direction information designated using the angle θ in the preoperative plan. In other words, the intraocular lens direction information G32 is presented such that the angle formed by the intraocular lens direction information G32 and a straight line 272 indicating the direction corresponding to the turning angle detection line 271 is equal to the angle θ obtained in advance.

Note that, although the presentation direction of the intraocular lens direction information is determined according to the turning angle of the eyeball in the example described above, the intraocular lens direction information may be displayed on the basis of the three-dimensional posture of the eyeball as the posture of the eye and on the basis of the preoperative plan. In this case, as appropriate according to the three-dimensional posture of the eyeball, a linear transformation is performed on the intraocular lens direction information for presentation. This not only presents the intraocular lens direction information in an appropriate direction, but also appropriately deforms the intraocular lens direction information according to the three-dimensional posture of the eyeball.

In addition, regarding the wound position information that is presented as the guide information, for example, if the position of a wound from the center of the eye, that is, the center of the corneal limbus, the size of the wound with respect to the corneal limbus, and the like are obtained as the preoperative planning information, it is possible to display the wound position information at a correct position using the preoperative planning information and the intraoperative posture of the eye.

Further, regarding the anterior capsule incision position information that is presented as the guide information, if the size of the anterior capsule incision position with respect to the corneal limbus is obtained as the preoperative planning information, the anterior capsule incision position information can be presented at an appropriate position on the basis of the preoperative planning information and the result of recognition of the intraoperative corneal range.

<Exemplary Configuration of Surgical System>

Next, a more detailed configuration of the portion of the above-described surgical system 11 for estimating the posture of a patient's eye and generating and presenting guide information will be described.

Figure 14:
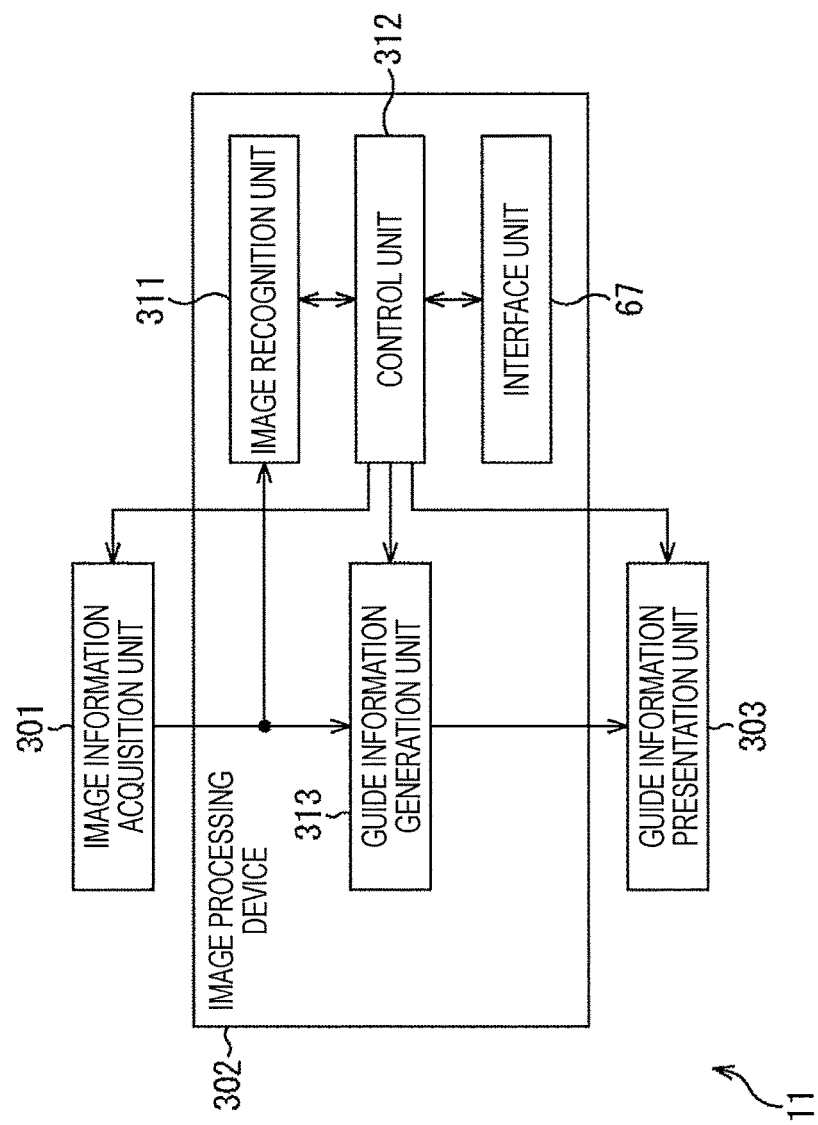
FIG. 14 is a diagram illustrating an exemplary configuration of the surgical system.

FIG. 14 is a diagram illustrating an exemplary configuration of the surgical system 11 that realizes such functions. Note that, in FIG. 14, a component corresponding to that in FIG. 2 is denoted by the same reference sign, and the description thereof is appropriately omitted.

In the example illustrated in FIG. 14, the surgical system 11 has an image information acquisition unit 301, an image processing device 302, and a guide information presentation unit 303.

The image information acquisition unit 301 acquires tomographic and front images and supplies them to the image processing device 302. Note that the image information acquisition unit 301 only needs to acquire at least a tomographic image and acquire a front image as necessary.

On the basis of the tomographic image supplied from the image information acquisition unit 301, the image processing device 302 obtains the posture of the patient's eye, generates guide information, and supplies it to the guide information presentation unit 303. At this time, the image processing device 302 may superimpose the guide information on the front image and supply it to the guide information presentation unit 303.

The guide information presentation unit 303 presents the guide information supplied from the image processing device 302. Here, the guide information presentation unit 303 includes, for example, the presentation unit 63, the monitor 33, and the like illustrated in FIG. 2.

Further, the image processing device 302 is realized, for example, by the control unit 66 and the interface unit 67 illustrated in FIG. 2.

The image processing device 302 has an image recognition unit 311, a control unit 312, the interface unit 67, and a guide information generation unit 313. Here, for example, the image recognition unit 311, the control unit 312, and the guide information generation unit 313 are realized when the control unit 66 illustrated in FIG. 2 executes a program.

The image recognition unit 311 performs image recognition on the tomographic and front images supplied from the image information acquisition unit 301, recognizes each part of the eye such as the angle positions, the boundary positions between the cornea and the sclera, the end point positions of the iris, the optic disc portion, and the fovea, and supplies the results of recognition to the control unit 312.

The interface unit 67 acquires, for example, preoperative tomographic and front images, preoperative planning information, and input instructions from a surgeon or the like, and supplies them to the control unit 312.

The control unit 312 controls each unit of the image processing device 302. For example, on the basis of the results of recognition of the respective parts of the eye supplied from the image recognition unit 311 and the preoperative tomographic image and preoperative planning information supplied from the interface unit 67, the control unit 312 recognizes the range of each part such as the corneal range and the posture of the eye, and instructs the guide information generation unit 313 to generate the guide information.

The guide information generation unit 313 generates the guide information according to the instruction from the control unit 312 using the front image supplied from the image information acquisition unit 301 as necessary, and supplies the guide information to the guide information presentation unit 303. As described above, the guide information may be information from which only a guide is superimposed and presented on an optical image of the eye of the patient, or may be image information that is superimposed on a front image. In a case where the guide information is superimposed on a front image, the guide information generation unit 313 generates a front image with the guide information superimposed thereon, and outputs it to the guide information presentation unit 303.

Figure 15:
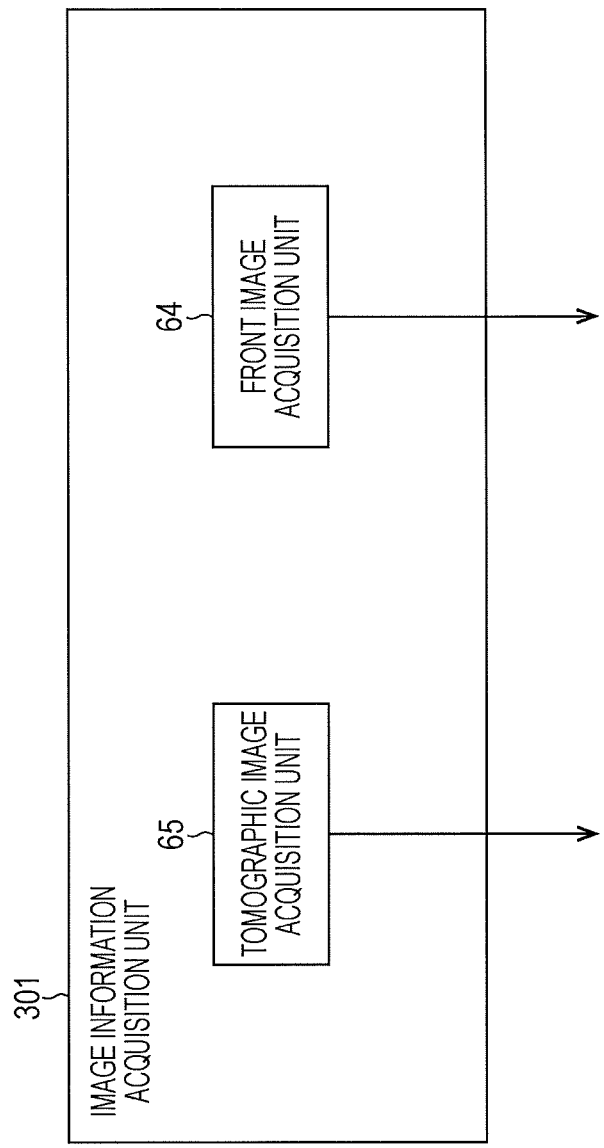
FIG. 15 is a diagram illustrating an exemplary configuration of an image information acquisition unit.

Further, in a case where the image information acquisition unit 301 acquires front and tomographic images, the image information acquisition unit 301 is configured as illustrated in FIG. 15, for example. Note that, in FIG. 15, a component corresponding to that in FIG. 2 is denoted by the same reference sign, and the description thereof is appropriately omitted.

The image information acquisition unit 301 illustrated in FIG. 15 includes the front image acquisition unit 64 and the tomographic image acquisition unit 65. In this example, the front image acquisition unit 64 photographs a front image and supplies it to the image recognition unit 311 and the guide information generation unit 313, and the tomographic image acquisition unit 65 photographs a tomographic image and supplies it to the image recognition unit 311.

Figure 16:
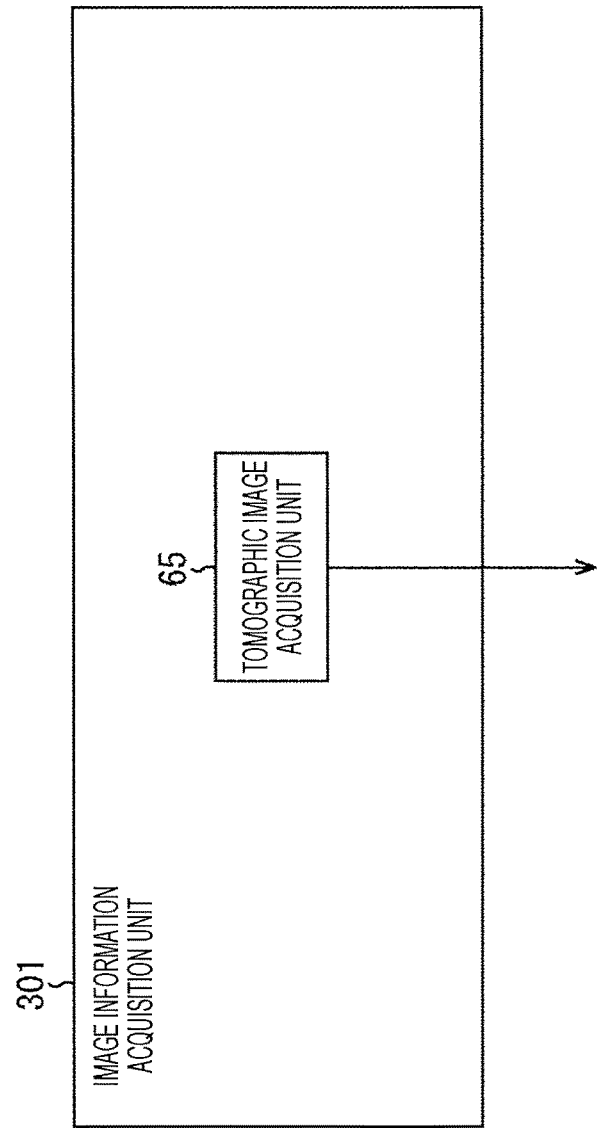
FIG. 16 is a diagram illustrating an exemplary configuration of the image information acquisition unit.

Alternatively, the image information acquisition unit 301 may be configured as illustrated in FIG. 16. Note that, in FIG. 16, a component corresponding to that in FIG. 2 is denoted by the same reference sign, and the description thereof is appropriately omitted.

The image information acquisition unit 301 illustrated in FIG. 16 includes the tomographic image acquisition unit 65. In this example, the tomographic image acquisition unit 65 photographs a tomographic image and supplies it to the image recognition unit 311, and the image information acquisition unit 301 does not photograph a front image.

<Description of Guide Information Presentation Process>

Next, the operation of the surgical system 11 illustrated in FIG. 14 will be described. Note that, in the following description, a case where guide information is presented (displayed) on the presentation unit 63 serving as the guide information presentation unit 303 will be described as an example.

In a case where cataract surgery is performed, the interface unit 67 acquires in advance a preoperative image that is a tomographic image taken before surgery and preoperative planning information, and supplies them to the control unit 312. Then, once the surgery is started, the surgical system 11 performs a guide information presentation process in each of a wound creation mode, an anterior capsule incision mode, and an intraocular lens insertion mode, and presents guide information.

As used herein, the wound creation mode is a mode of presenting wound position information as a guide for use by a surgeon in creating a wound, and the anterior capsule incision mode is a mode of presenting anterior capsule incision position information as a guide for use by a surgeon in incising the anterior capsule. In addition, the intraocular lens insertion mode is a mode of presenting intraocular lens direction information as a guide for use by a surgeon in inserting an intraocular lens into the crystalline lens.

The surgical system 11 performs the guide information presentation process in each mode while appropriately switching the mode. Specifically, after the guide information presentation process is initially performed in the wound creation mode, the guide information presentation process is performed in the anterior capsule incision mode, and the guide information presentation process is further performed in the intraocular lens insertion mode. For example, the mode may be switched when a surgeon or the like operates the interface unit 67, or may be performed by the surgical system 11 on the basis of a front image or the like.

Here, with reference to the flowchart of FIG. 17, the guide information presentation process that is performed by the surgical system 11 will be described using the case of the wound creation mode as an example.

In step S11, the image information acquisition unit 301 acquires image information. Specifically, the tomographic image acquisition unit 65 of the image information acquisition unit 301 takes, at respective cross-sectional positions, intraoperative images which are tomographic images photographed during surgery, and supplies them to the image recognition unit 311.

In step S12, the image recognition unit 311 performs image recognition on the intraoperative images supplied from the tomographic image acquisition unit 65 or on the volume data including the tomographic images as the intraoperative images, recognizes the positions of the respective parts of the eye, and supplies the results of recognition to the control unit 312.

In step S12, for example, the positions of the respective parts such as the angle positions, the boundary positions between the cornea and the sclera, the end point positions of the iris, the position of the optic disc, and the position of the fovea are recognized in the tomographic images as the intraoperative images or in the volume data.

In step S13, the control unit 312 obtains the posture of the patient's eye on the basis of the results of recognition supplied from the image recognition unit 311 and the preoperative image supplied from the interface unit 67. For example, the control unit 312 obtains the corneal and pupil ranges of the eye as appropriate according to the above-described methods indicated in (A) to (C), and further obtains the posture of the eye according to the above-described method indicated in (D) or (E).

Here, in the preoperative image supplied from the interface unit 67, the positions of the corneal range, pupil range, optic disc, fovea, turning angle detection line, sclera, retina, and the like and the distribution of the blood vessels are obtained in advance by means of image recognition or the like on the tomographic image photographed as the preoperative image before surgery. In other words, the parts and posture of the preoperative eye are obtained for use as a reference.

In step S14, the control unit 312 designates the guide information to be presented according to the current mode. For example, since the current mode is the wound creation mode in this example, corneal limbus information and wound position information are designated as the guide information to be presented.

Upon designating the guide information to be presented, the control unit 312 supplies various kinds of information necessary for generating the guide information to the guide information generation unit 313, and instructs the guide information generation unit 313 to generate the guide information.

For example, in this example, the control unit 312 supplies, to the guide information generation unit 313, information indicating the corneal range obtained as the result of image recognition and supplied from the image recognition unit 311, and instructs the guide information generation unit 313 to generate the corneal limbus information as the guide information.

Further, the control unit 312 obtains the position at which the wound position information is to be presented at the current time on the basis of the posture of the eye obtained in the process of step S13, the positions and ranges of the respective parts of the eye such as the corneal range, and the information, supplied from the interface unit 67, indicating the presentation position of the wound position information as the preoperative planning information. At this time, the control unit 312 may perform a linear transformation in accordance with the posture of the eyeball to deform the shape of the wound position information.

The control unit 312 supplies the information, obtained in the above-mentioned manner, indicating the position at which the wound position information is to be presented to the guide information generation unit 313, and instructs the guide information generation unit 313 to generate the wound position information as the guide information.

In step S15, the guide information generation unit 313 generates the guide information according to the instruction from the control unit 312, and supplies it to the guide information presentation unit 303. In this example, the guide information generation unit 313 generates the corneal limbus information and the wound position information on the basis of the information supplied from the control unit 312.

In step S16, the presentation unit 63 of the guide information presentation unit 303 presents the guide information supplied from the guide information generation unit 313. Consequently, for example, the corneal limbus information G11 and the wound position information G12 illustrated in FIG. 7 are superimposed and presented on an optical image of the eye of the patient.

Note that the corneal limbus information and the wound position information may be superimposed on a front image in the monitor 33. In such a case, the guide information generation unit 313 superimposes the generated corneal limbus information and wound position information on the front image supplied from the front image acquisition unit 64 of the image information acquisition unit 301, and supplies it to the monitor 33 serving as the guide information presentation unit 303.

In step S17, the control unit 312 determines whether to end the process. It is determined to end the process in a case where an instruction to end the presentation of the guide information is given, such as when an instruction to switch from the current mode to the next mode is given.

If it is determined in step S17 not to end the process, the process returns to step S11, and the above-described process is repeatedly performed.

On the other hand, if it is determined in step S17 to end the process, the guide information presentation process is ended.

In the above-mentioned manner, the surgical system 11 recognizes each part of the eye on the basis of the tomographic images of the eye of the patient, and obtains the posture of the eye on the basis of the result of recognition. Then, the surgical system 11 generates and presents the guide information on the basis of the obtained posture of the eye.

As described above, by recognizing each part of the eye on the basis of the tomographic images and obtaining the posture of the eye, it is possible to obtain the posture of the eye more firmly and with a high degree of accuracy. As a result, it is possible to present the guide information with a higher degree of accuracy.

The guide information presentation process in the case of the wound creation mode has been described in detail so far. Note that in the case of the anterior capsule incision mode and in the case of the intraocular lens insertion mode, processes similar to the guide information presentation process described with reference to FIG. 17 are performed.

For example, in the case of the anterior capsule incision mode, in step S14, as in the case of the wound creation mode, the control unit 312 supplies the information indicating the corneal range to the guide information generation unit 313, and instructs the guide information generation unit 313 to generate the corneal limbus information as the guide information.

In addition, the control unit 312 obtains the position at which the anterior capsule incision position information is to be presented at the current time on the basis of the corneal limbus determined from the corneal range at the current time and the information, supplied from the interface unit 67, indicating the size of the anterior capsule incision position with respect to the corneal limbus as the preoperative planning information. At this time, the control unit 312 may perform a linear transformation in accordance with the posture of the eyeball to deform the shape of the anterior capsule incision position information.

The control unit 312 supplies the information, obtained in the above-mentioned manner, indicating the position at which the anterior capsule incision position information is to be presented to the guide information generation unit 313, and instructs the guide information generation unit 313 to generate the anterior capsule incision position information as the guide information. Then, in step S15, the guide information generation unit 313 generates the corneal limbus information and the anterior capsule incision position information as the guide information according to the instruction from the control unit 312.

In addition, for example, in the case of the intraocular lens insertion mode, in step S14, as in the case of the wound creation mode, the control unit 312 supplies the information indicating the corneal range to the guide information generation unit 313, and instructs the guide information generation unit 313 to generate the corneal limbus information as the guide information.

Further, the control unit 312 obtains the direction in which the intraocular lens direction information is to be presented at the current time on the basis of the turning angle obtained as the posture of the eye in the process of step S13 and the angle $\theta$ supplied from the interface unit 67 as the preoperative planning information. At this time, the control unit 312 may perform a linear transformation in accordance with the posture of the eyeball to deform the shape of the intraocular lens direction information.

The control unit 312 supplies the information, obtained in the above-mentioned manner, indicating the direction in which the intraocular lens direction information is to be presented to the guide information generation unit 313, and instructs the guide information generation unit 313 to generate the intraocular lens direction information as the guide information. Then, in step S15, the guide information generation unit 313 generates the corneal limbus information and the intraocular lens direction information as the guide information according to the instruction from the control unit 312.

Second Embodiment

<Regarding Image Recognition>

Figure 18:
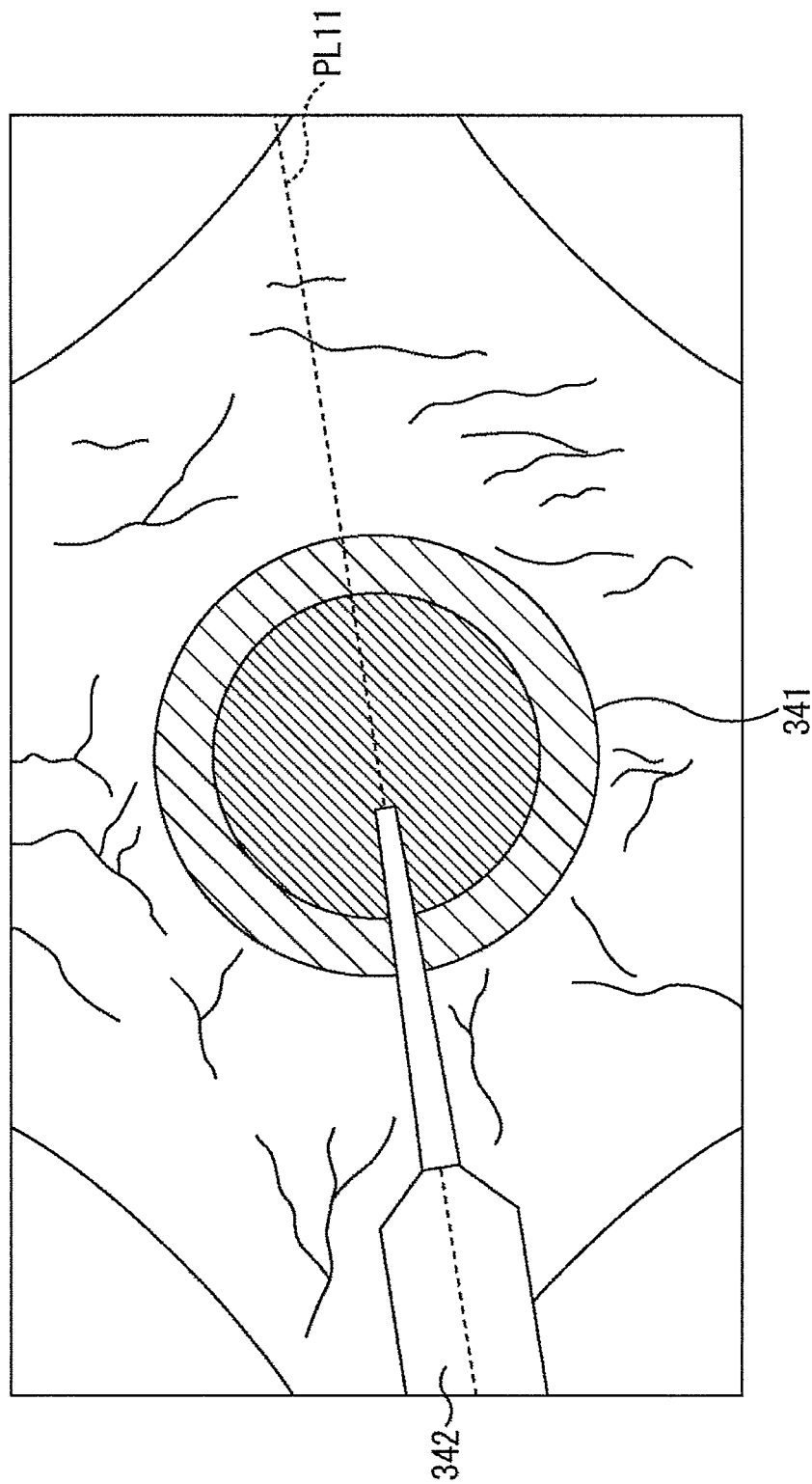
FIG. 18 is a diagram for explaining the influence of a surgical tool on image recognition.
Figure 19:
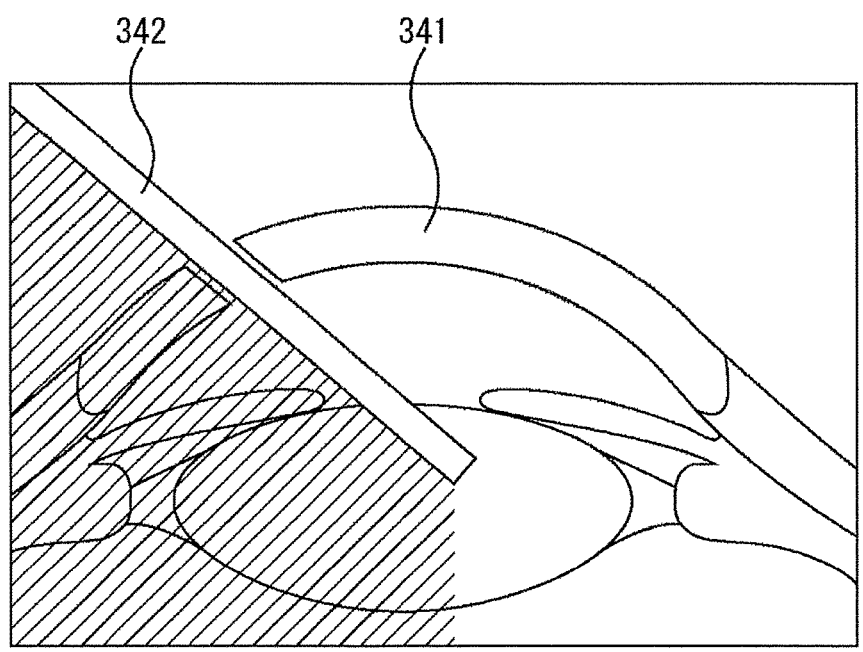
FIG. 19 is a diagram for explaining the influence of the surgical tool on image recognition.

Meanwhile, during surgery, since a surgeon performs the surgery using a surgical tool as illustrated, for example, in FIG. 18, it is not possible to acquire tomographic information in the shadow part of the surgical tool as illustrated in FIG. 19. Note that, in FIG. 19, a component corresponding to that in FIG. 18 is denoted by the same reference sign, and the description thereof is appropriately omitted. Further, FIG. 19 is a cross-sectional view taken along a dotted line PL11 on the patient's eye illustrated in FIG. 18.

In the example illustrated in FIG. 18, the surgeon inserts a surgical tool 342 into the crystalline lens through a part of a cornea 341 of the patient's eye to perform the surgery. Therefore, in a case where a tomographic image is photographed in such a state, the depth side portion of the surgical tool 342 in the drawing is in shadow.

Specifically, as illustrated in FIG. 19, the part below the surgical tool 342 in the drawing is in shadow. Then, a region in the tomographic image corresponding to that part is darkened or blurred, and useful information cannot be obtained. In other words, it is difficult to recognize each part of the patient's eye in the shadow part of the surgical tool 342.

Therefore, the shadow part of the surgical tool in the tomographic image may not be used for image recognition. In such a case, for example, the image information acquisition unit 301 is configured as illustrated in FIG. 15, and a front image photographed by the front image acquisition unit 64 is supplied to the image recognition unit 311. Specifically, in the process of step S11 described with reference to FIG. 17, a front image is also acquired.

Then, in step S12, the image recognition unit 311 first performs image recognition on the front image. In the image recognition on the front image, the region other than the eye of the patient, e.g., the region of the surgical tool, is recognized from the front image by means of image recognition or the like using a dictionary or the like registered in advance. Then, the region in the shadow of the surgical tool in the tomographic image is specified on the basis of the result of recognition.

Specifically, the region of the surgical tool in the tomographic image can be specified from the result of recognition of the region of the surgical tool in the front image. Therefore, in the tomographic image, the region located on the depth side of the region of the surgical tool in the front direction, that is, the region located on the foveal side as viewed from the cornea, is specified as the region in the shadow of the surgical tool. Note that the process of specifying the region in the shadow of the surgical tool in the tomographic image may be performed by the image recognition unit 311 or may be performed by the control unit 312.

Furthermore, the image recognition unit 311 recognizes the position of each part of the eye by means of image recognition on the basis of tomographic images and the volume data obtained from the tomographic images while excluding the regions in the shadow of the surgical tool in the tomographic images.

Note that, in the above description, the region in the shadow of the surgical tool in the tomographic image is estimated from the result of recognition of the region of the surgical tool in the front image. However, a method of estimating the region in the shadow of the surgical tool only from the tomographic image may be employed using information about the surgical tool obtained in the tomographic image, e.g., information on the position of strong reflection by the surgical tool or the like.

In this way, by using only the useful region in the tomographic image when recognizing the position of each part of the eye of the patient, it is possible to obtain the posture of the eye more firmly and with a high degree of accuracy.

Third Embodiment

<Regarding Acquisition of Tomographic Image>

Further, by using a front image, the positions of the cornea and pupil can be roughly specified by means of image recognition. Therefore, in a case where the image information acquisition unit 301 is configured as illustrated in FIG. 15, the cross-sectional position for acquiring a tomographic image may be designated on the basis of a front image.

For example, the fovea and the optic disc are located in the vicinity of the center of the pupil, that is, in the vicinity of the eye axis, when the eye is viewed in the front direction. Therefore, in a case where the positions of the optic disc and fovea are recognized from tomographic images or volume data, and the posture of the eye is obtained using the results of recognition, the posture of the eye can be obtained more efficiently if an appropriate cross-sectional position is specified from a front image, and if a tomographic image is acquired in accordance with the result of specification.

Figure 20:
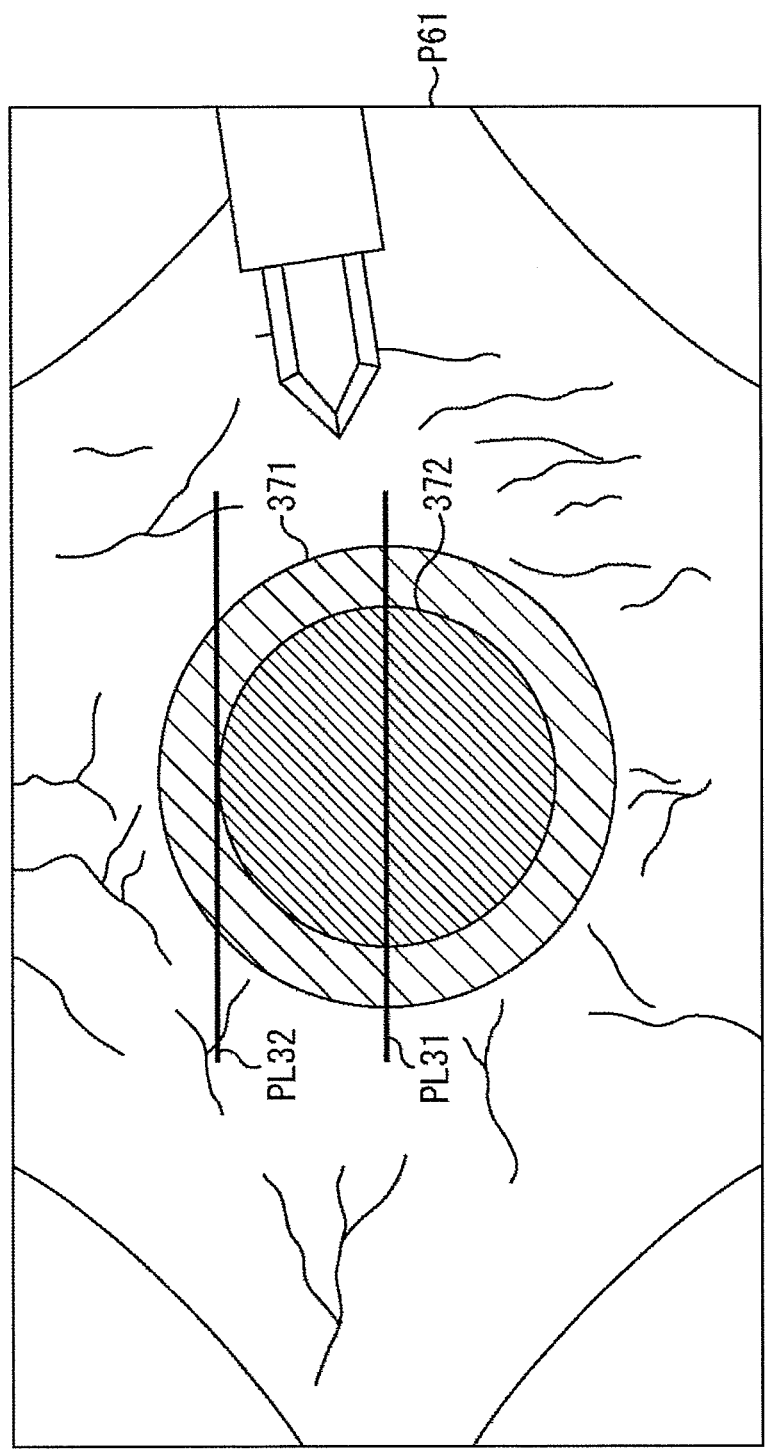
FIG. 20 is a diagram for explaining a cross-sectional position for acquiring a tomographic image.

For example, it is assumed that a front image P61 is acquired during surgery by the front image acquisition unit 64 constituting the image information acquisition unit 301 as illustrated in FIG. 20.

In this case, from the front image P61, the range of a cornea 371 and the range of a pupil 372 can be estimated by means of image recognition. Further, if a tomographic image is acquired at the cross-sectional position including a straight line PL31 passing near the center of the cornea 371 and pupil 372, the tomographic image is most likely to contain the fovea and the optic disc. On the other hand, if a tomographic image is acquired at the cross-sectional position including a straight line PL32 passing near the edge of the cornea 371 and pupil 372, the tomographic image is unlikely to contain the fovea and the optic disc.

Therefore, it is preferable that the range of the cornea 371 and the range of the pupil 372 be estimated from the front image P61, tomographic images be acquired at one or more appropriate cross-sectional positions such as the cross-sectional position including the straight line PL31 by using the results of estimation, and no tomographic image be acquired at the cross-sectional position including the straight line PL32.

In such a case, in step S11 of the guide information presentation process described with reference to FIG. 17, an intraoperative front image is first acquired by the front image acquisition unit 64 constituting the image information acquisition unit 301, and supplied to the image recognition unit 311.

Then, the image recognition unit 311 performs image recognition on the front image supplied from the front image acquisition unit 64, recognizes each part of the eye such as the corneal range and the pupil range, and supplies the results of recognition to the control unit 312.

Further, the control unit 312 designates the cross-sectional position for acquiring a tomographic image on the basis of the results of recognition of the respective parts such as the corneal range and the pupil range in the front image supplied from the image recognition unit 311, and controls the tomographic image acquisition unit 65 of the image information acquisition unit 301 in accordance with the designation. In this case, for example, the cross-sectional position including the straight line PL31 illustrated in FIG. 20 and some cross-sectional positions in the vicinity of the cross-sectional position are designated as the cross-sectional positions at which tomographic images are to be acquired. When the control unit 312 controls the tomographic image acquisition unit 65 in this manner, the control unit 312 functions as an acquisition control unit.

Under the control of the control unit 312, the tomographic image acquisition unit 65 acquires tomographic images at one or more cross-sectional positions designated by the control unit 312, and supplies the tomographic images to the image recognition unit 311.

In this way, if an appropriate cross-sectional position is designated on the basis of the information obtained from the front image, the posture of the patient's eye can be obtained more efficiently.

Fourth Embodiment

<Regarding Improvement in Accuracy of Image Recognition with Front Image>

Furthermore, in a case where the image information acquisition unit 301 is configured as illustrated in FIG. 15, the positions of the cornea and pupil can be roughly specified from a front image photographed during surgery by means of image recognition. Therefore, a detection range for each part of the eye from a tomographic image may be determined using the results of specification, and the position of each part of the eye may be detected (recognized) from the tomographic image by means of image recognition on the detection range.

Figure 21:
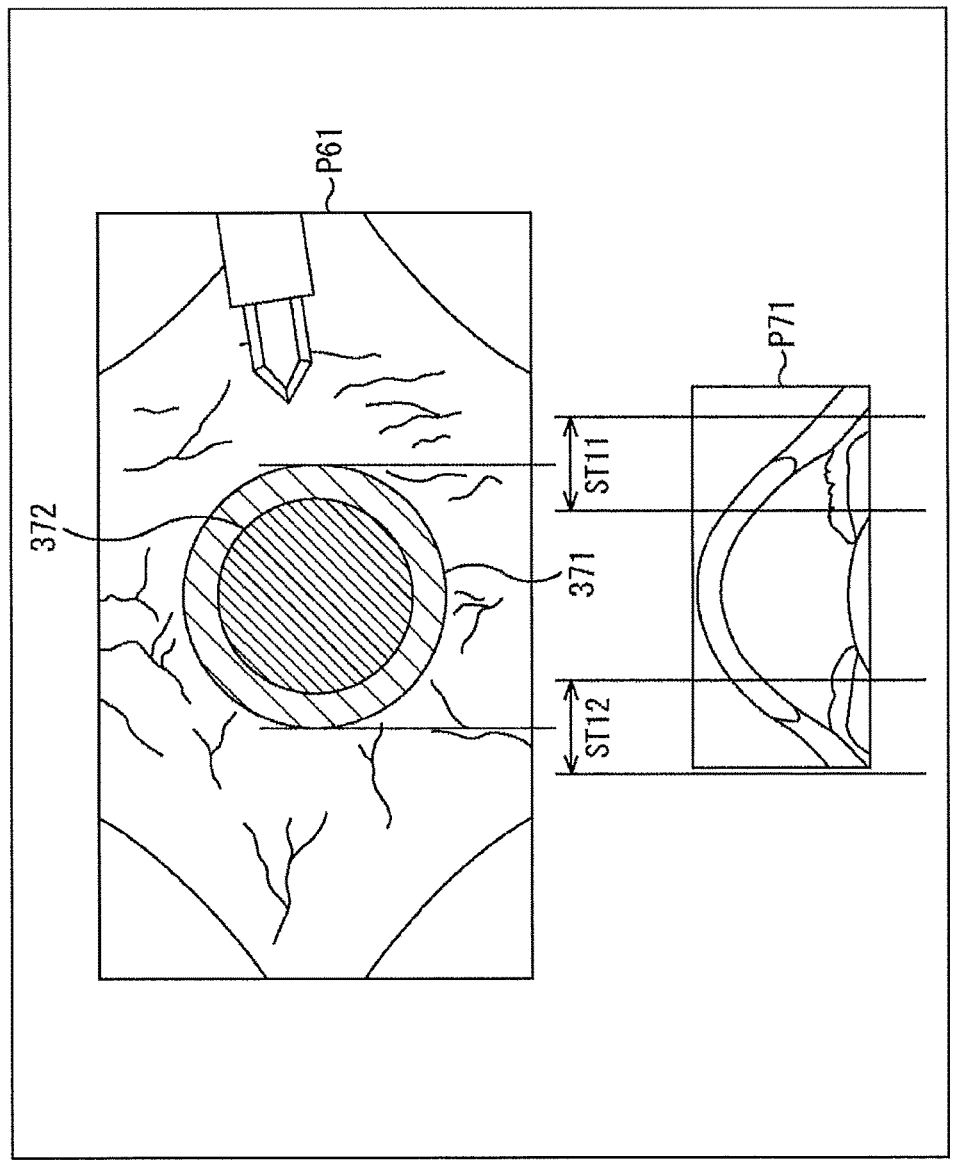
FIG. 21 is a diagram for explaining image recognition with front and tomographic images.

For example, as illustrated in FIG. 21, it is assumed that the front image P61 and a tomographic image P71 are photographed during surgery. Note that, in FIG. 21, a component corresponding to that in FIG. 20 is denoted by the same reference sign, and the description thereof is appropriately omitted.

In FIG. 21, the front image P61 indicates a front image acquired by the front image acquisition unit 64 during surgery, and the tomographic image P71 indicates a tomographic image photographed by the tomographic image acquisition unit 65 at the same time or substantially at the same time as the front image P61.

Consider, for example, a case where the image recognition unit 311 performs image recognition for recognizing the angle positions from the tomographic image P71. In this case, the image recognition unit 311 first performs image recognition on the front image P61 and recognizes the cornea 371 from the front image P61.

Then, in the tomographic image P71, the image recognition unit 311 designates a detection range ST11 and a detection range ST12, each of which is a region having a predetermined width including the position corresponding to the end portion of the cornea 371, as the regional ranges in which the angle positions are recognized. This is because the angle is located near the end portion of the cornea.

Using only the regions of the detection range ST11 and the detection range ST12 designated in this manner as the processing targets, the image recognition unit 311 recognizes the angle positions from the tomographic image P71 by means of image recognition. Then, for example, the control unit 312 recognizes the corneal range on the basis of the results of recognition of the angle positions from the tomographic image P71 or the like.

As described above, in the case where the detection range for image recognition on the tomographic image is designated on the basis of the information obtained from the front image, in the guide information presentation process described with reference to FIG. 17, front and tomographic images are acquired as the image information in step S11.

Then, in step S12, the image recognition unit 311 performs image recognition on the front image supplied from the front image acquisition unit 64, recognizes each part of the eye, and designates, in the tomographic image on the basis of the result of recognition, the detection range for each part of the eye to be recognized.

Further, the image recognition unit 311 performs image recognition on the tomographic image supplied from the tomographic image acquisition unit 65 using only the region of the designated detection range as the processing target, and recognizes the position of each part of the eye on the tomographic image.

At this time, in the image recognition that is performed on the front image in order to designate the detection range for recognizing the part of the eye on the tomographic image, the part of the eye to be recognized through the image recognition may be the same as or different from the part of the eye to be recognized in the tomographic image.

In this manner, by designating the detection range from the information obtained from the front image, and recognizing the position of each part of the eye on the tomographic image using the detection range as the target, it is possible to improve the recognition accuracy for the position of each part of the eye in the tomographic image.

Note that, although the position of each part of the eye on the tomographic image is recognized in the example described above, the detection range may be designated in volume data obtained from tomographic images on the basis of a front image, and the position of each part of the eye may be recognized from the detection range in the volume data.

Fifth Embodiment

<Regarding Improvement in Accuracy of Image Recognition with Front Image>

Meanwhile, the blood vessels and iris of the eye included as a subject in a front image are useful information for accurately grasping the positional relationship between the intraoperative and preoperative eyes, that is, the posture of the eye, as long as the positions of the blood vessels and iris in the front image can be recognized precisely.

Therefore, the posture of the eye may be obtained with a higher degree of accuracy by using both tomographic and front images. Specifically, for example, in a case where the image information acquisition unit 301 is configured as illustrated in FIG. 15, the posture of the eye may be grasped with a coarse degree of accuracy on the basis of the tomographic images, and the final posture of the eye may be further obtained with a higher degree of accuracy on the basis of the front images.

For example, suppose that the turning angle is obtained as the posture of the eye. In such a case, first, the turning angle indicating the posture of the eye is obtained from a tomographic image acquired before surgery and a tomographic image acquired during surgery. As a result, it is assumed that a turning angle $\theta_1$ is obtained as illustrated by an arrow A71 in FIG. 22, for example.

Figure 22:
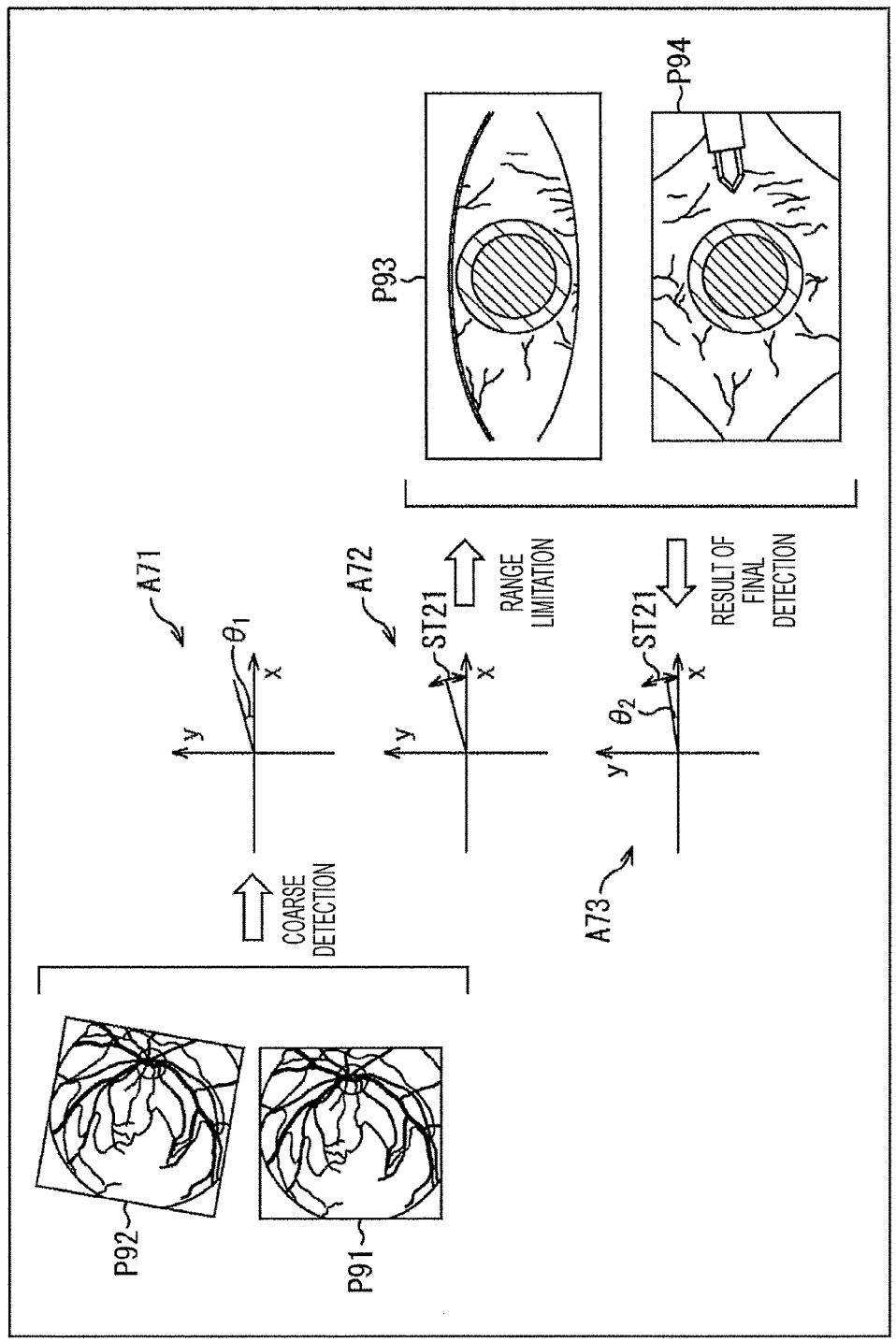
FIG. 22 is a diagram for explaining image recognition with front and tomographic images.

In the example illustrated in FIG. 22, the turning angle $\theta_1$ obtained as the coarse detection on the basis of the preoperative and intraoperative tomographic images indicates the rotation angle of the turning angle detection line in a reconstructed front image P92 reconstructed from the intraoperative tomographic image with respect to the turning angle detection line in a reconstructed front image P91 reconstructed from the preoperative tomographic image.

Once the turning angle $\theta_1$ is obtained in this manner, a detection range ST21 for the turning angle for use with front images is designated on the basis of the turning angle $\theta_1$ as illustrated by an arrow A72. Specifically, the detection range for the turning angle for use with front images is limited within a reasonable range for the posture of the eye determined from the posture of the eye calculated on the basis of the tomographic images. Specifically, for example, a predetermined angular range around the turning angle $\theta_1$ is designated as the detection range ST21.

Then, as illustrated by an arrow A73, within the detection range ST21 designated on the basis of the turning angle $\theta_1$, a final turning angle $\theta_2$ is obtained from a front image P93 acquired before surgery and a front image P94 acquired during surgery. Here, the turning angle $\theta_2$ is always within the detection range ST21 designated on the basis of the turning angle $\theta_1$.

To obtain the turning angle $\theta_2$ on the basis of the front images, each part of the eye such as the blood vessels and the iris recognized by means of image recognition from the front images is used. Specifically, the positional relationship of each part of the eye is obtained by means of matching, and the turning angle $\theta_2$ is obtained from the positional relationship obtained as the result of matching. At this time, the front image P93 is rotated within the detection range ST21, and the rotation angle of the front image P93 obtained when the respective parts of the eye on the front image P93 overlap the corresponding parts of the eye on the front image P94 acquired during surgery is regarded as the turning angle $\theta_2$.

In this way, by obtaining the turning angle as the posture of the eye on the basis of the tomographic images, and further obtaining the final turning angle from the turning angle and the front images, it is possible to obtain the turning angle as the posture of the eye with a higher degree of accuracy. As a result, the guide information can be presented more firmly and with a high degree of accuracy.

Figure 17:
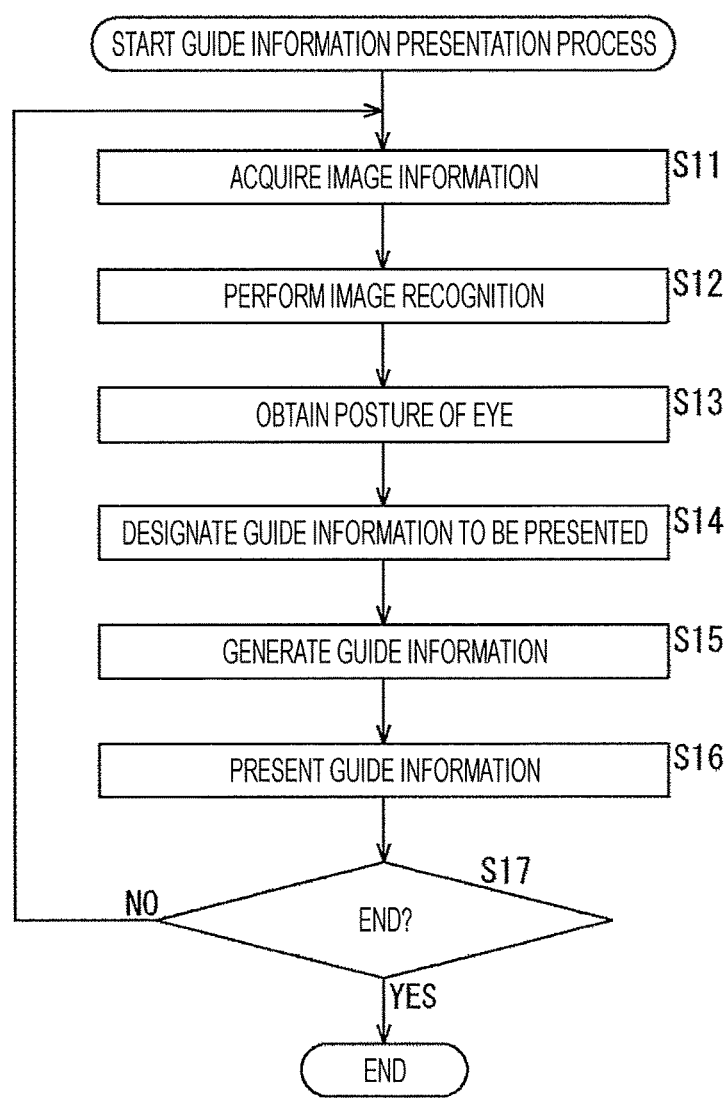
FIG. 17 is a flowchart for explaining a guide information presentation process.

Note that in the case where the posture of the eye is obtained on the basis of the tomographic and front images, before the guide information presentation process described with reference to FIG. 17 is started in the surgical system 11, preoperative tomographic and front images and preoperative planning information are acquired in advance by the interface unit 67 and supplied to the control unit 312.

Then, in step S11, intraoperative front and tomographic images are acquired by the front image acquisition unit 64 and the tomographic image acquisition unit 65 of the image information acquisition unit 301 and supplied to the image recognition unit 311.

In addition, in step S12, the image recognition unit 311 performs image recognition on the intraoperative front image supplied from the front image acquisition unit 64 to recognize each part such as the blood vessels and the iris, and performs image recognition on the tomographic image supplied from the tomographic image acquisition unit 65 to recognize the position of each part of the eye. Then, the image recognition unit 311 supplies the result of recognition of each part from the front image and the result of recognition of each part from the tomographic image to the control unit 312.

Furthermore, in step S13, the control unit 312 obtains the turning angle as the posture of the eye of the patient on the basis of the result of recognition of each part from the tomographic image supplied from the image recognition unit 311 and the preoperative tomographic image supplied from the interface unit 67. Further, the control unit 312 designates, from the obtained turning angle, the detection range for use with front images for detecting the turning angle.

On the basis of the result of recognition of each part from the front image supplied from the image recognition unit 311 and the preoperative front image supplied from the interface unit 67, the control unit 312 obtains the turning angle of the eye within the designated detection range as the final posture of the patient's eye.

Note that, although the turning angle is obtained as the posture of the eye in the example described above, even in the case of obtaining the three-dimensional posture of the eye as the posture of the eye, it is possible to perform a process similar to the process described above to obtain the posture of the eye with a higher degree of accuracy.

Meanwhile, the above-mentioned sequence of processes can be executed by hardware, and can also be executed by software. In a case where the sequence of processes is executed by the software, a program constituting the software is installed on a computer. As used herein, the computer includes a computer incorporated in dedicated hardware or, for example, a general personal computer or the like that can install various programs to execute various functions.

Figure 23:
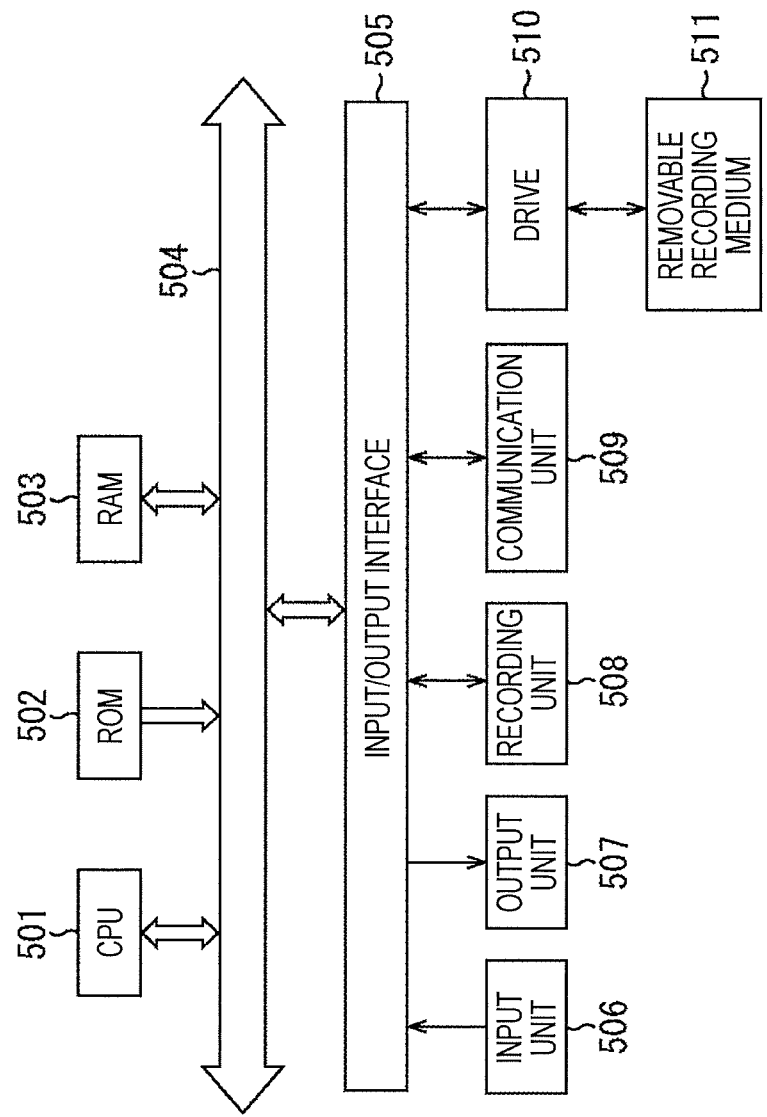
FIG. 23 is a diagram illustrating an exemplary configuration of a computer.

FIG. 23 is a block diagram illustrating an exemplary configuration of the hardware of the computer that executes the above-mentioned sequence of processes by means of the program.

In the computer, a central processing unit (CPU) 501, a read only memory (ROM) 502, and a random access memory (RAM) 503 are coupled to one another by a bus 504.

An input/output interface 505 is further connected to the bus 504. An input unit 506, an output unit 507, a recording unit 508, a communication unit 509, and a drive 510 are connected to the input/output interface 505.

The input unit 506 includes a keyboard, a mouse, a microphone, an image sensor, and the like. The output unit 507 includes a display, a speaker, and the like. The recording unit 508 includes a hard disc, a non-volatile memory, and the like. The communication unit 509 includes a network interface and the like. The drive 510 drives a removable recording medium 511 such as a magnetic disc, an optical disc, a magneto-optical disc, or a semiconductor memory.

In the computer configured as mentioned above, the CPU 501 loads, for example, the program recorded in the recording unit 508 on the RAM 503 via the input/output interface 505 and the bus 504, and executes the program, whereby the above-mentioned sequence of processes is performed.

The program that is executed by the computer (CPU 501) can be recorded in the removable recording medium 511 serving as, for example, a package medium or the like, and provided. Alternatively, the program can be provided through a wired or wireless transmission medium such as a local area network, the Internet, and digital satellite broadcasting.

In the computer, the program can be installed on the recording unit 508 via the input/output interface 505 when the removable recording medium 511 is mounted in the drive 510. Alternatively, the program can be received at the communication unit 509 via a wired or wireless transmission medium, and installed on the recording unit 508. Additionally, the program can be installed in advance on the ROM 502 or the recording unit 508.

Note that the program that is executed by the computer may be such a program that the processes are performed in time series in the order described in the present description, or may be such a program that the processes are performed parallelly or at a necessary timing, i.e., when a call is performed, for example.

Note that the embodiment of the present technology is not limited to the above-mentioned embodiments, and can be variously changed in a range not departing from the gist of the present technology.

For example, the present technology can take a configuration of cloud computing in which a single function is shared and processed by a plurality of devices in cooperation with each other via a network.

In addition, the respective steps described in the above-mentioned flowchart can be executed by a single device, or can be shared and executed by a plurality of devices.

Furthermore, in a case where a plurality of processes is included in a single step, the plurality of processes included in the single step can be executed by a single device, or can be shared and executed by a plurality of devices.

Furthermore, the present technology can be configured as follows.

(1)

A surgical system including:

a tomographic image acquisition unit configured to acquire a tomographic image that is a cross-sectional image taken in a direction substantially parallel to an eye axis direction of an eye that is a surgical target;

an image recognition unit configured to recognize a predetermined part of the eye in the tomographic image on the basis of the tomographic image; and a posture calculation unit configured to calculate a posture of the eye on the basis of a result of recognition of the predetermined part.

(2)

The surgical system according to (1), further including a front image acquisition unit configured to photograph the eye that is the surgical target substantially in the eye axis direction.

(3)

The surgical system according to (2), in which the posture calculation unit calculates the posture of the eye on the basis of the result of recognition of the predetermined part and a front image obtained by the front image acquisition unit.

(4)

An image processing device including:

an image recognition unit configured to recognize, on the basis of a tomographic image that is a cross-sectional image taken in a direction substantially parallel to an eye axis direction of an eye that is a surgical target, a predetermined part of the eye in the tomographic image; and a posture calculation unit configured to calculate a posture of the eye on the basis of a result of recognition of the predetermined part.

(5)

The image processing device according to (4), in which the posture calculation unit calculates, as the posture of the eye, a turning angle of the eye around the eye axis serving as a rotation axis.

(6)

The image processing device according to (4), in which the posture calculation unit calculates a three-dimensional posture of the eye.

(7)

The image processing device according to (6), in which the posture calculation unit calculates the three-dimensional posture of the eye on the basis of an amount of rotation of the eye.

(8)

The image processing device according to any one of (5) to (7), in which the posture calculation unit calculates the posture of the eye on the basis of a positional relationship between an optic disc and a fovea recognized as the predetermined part.

(9)

The image processing device according to any one of (4) to (8), in which the image recognition unit recognizes the predetermined part of the eye on the basis of the tomographic image of the eye taken before or during surgery.

(10)

The image processing device according to any one of (4) to (9), in which the image recognition unit recognizes, on the basis of a front image obtained by photographing the eye substantially in the eye axis direction, a specific part of the eye in the front image, and the image recognition unit recognizes the predetermined part in the tomographic image using, as a target, a region on the tomographic image designated by applying a result of recognition of the specific part.

(11)

The image processing device according to any one of (4) to (9), in which the posture calculation unit calculates a final posture of the eye on the basis of a result of calculation of the posture of the eye that is based on the result of recognition of the predetermined part and on the basis of a front image obtained by photographing the eye substantially in the eye axis direction.

(12)

The image processing device according to (11), in which the posture calculation unit calculates the final posture of the eye on the basis of the front image within a range of posture designated by applying the result of calculation of the posture of the eye that is based on the result of recognition of the predetermined part.

(13)

The image processing device according to any one of (4) to (9), in which the image recognition unit recognizes, on the basis of a front image obtained by photographing the eye substantially in the eye axis direction, a specific part of the eye in the front image, and the image processing device further includes an acquisition control unit configured to operate such that the tomographic image at a cross-sectional position designated by applying a result of recognition of the specific part is acquired.

(14)

The image processing device according to any one of (4) to (9), in which the image recognition unit recognizes, on the basis of a front image obtained by photographing the eye substantially in the eye axis direction during surgery on the eye, a surgical tool on the front image, and recognizes the predetermined part while excluding a region on the tomographic image designated by applying a result of recognition of the surgical tool.

(15)

The image processing device according to any one of (4) to (9), in which the image recognition unit recognizes the predetermined part in volume data obtained from a plurality of the tomographic images taken at different cross-sectional positions.

(16)

The image processing device according to any one of (4) to (15), further including a guide information generation unit configured to generate, on the basis of the posture of the eye, guide information as a guide for use in surgery on the eye.

(17)

The image processing device according to any one of (4) to (16), in which the tomographic image is an image photographed with an optical coherence tomography device.

(18)

An image processing method including the steps of:

recognizing, on the basis of a tomographic image that is a cross-sectional image taken in a direction substantially parallel to an eye axis direction of an eye that is a surgical target, a predetermined part of the eye in the tomographic image; and calculating a posture of the eye on the basis of a result of recognition of the predetermined part.

REFERENCE SIGNS LIST

11 Surgical system
21 Surgical microscope
33 Monitor
63 Presentation unit
64 Front image acquisition unit
65 Tomographic image acquisition unit
66 Control unit
67 Interface unit
301 Image information acquisition unit
302 Image processing device
303 Guide information presentation unit
311 Image recognition unit
312 Control unit
313 Guide information generation unit

The invention claimed is:

1. A surgical system, comprising:
a first imaging device; and
processing circuitry configured to
acquire, via the first imaging device, a tomographic image of an eye,
recognize a predetermined part in a posterior segment of the eye in the acquired tomographic image, and
calculate a posture of the eye based on the recognized predetermined part in the posterior segment of the eye in the acquired tomographic image,
wherein the acquired tomographic image is a cross-sectional image acquired in a direction parallel to an eye axis.

2. The surgical system according to claim 1, wherein the processing circuitry is further configured to
photograph, via a second imaging device, the eye along the eye axis.

3. The surgical system according to claim 2, wherein the processing circuitry is further configured to
calculate the posture of the eye based on the recognized predetermined part in the posterior segment of the eye in the acquired tomographic image and a front image acquired via the second imaging device.

4. A device, comprising:
processing circuitry configured to
recognize, based on a tomographic image of an eye acquired, via a first imaging device, in a direction parallel to an eye axis of the eye, a predetermined part in a posterior segment of the eye, and
calculate a posture of the eye based on the recognized predetermined part in the posterior segment of the eye in the acquired tomographic image,
wherein the acquired tomographic image is a cross-sectional image.

5. The device according to claim 4, wherein the calculated posture of the eye is a turning angle of the eye around the eye axis serving as a rotation axis.

6. The device according to claim 4, wherein the calculated posture of the eye is a three-dimensional posture of the eye.

7. The device according to claim 6, wherein the three-dimensional posture of the eye is calculated based on an amount of rotation of the eye.

8. The device according to claim 5, wherein the calculated posture of the eye is based on a positional relationship between an optic disc of the eye and a fovea of the eye, the optic disc of the eye and the fovea of the eye being recognized as the predetermined part in the posterior segment of the eye in the acquired tomographic image.

9. The device according to claim 4, wherein the tomographic image is acquired pre-operatively and/or intra-operatively.

10. The device according to claim 4, wherein the processing circuitry is further configured to
recognize a specific part in a front image of the eye acquired, via a second imaging device, along the eye axis,
wherein the predetermined part in the posterior segment of the eye in the acquired tomographic image is recognized by using, as a target, a region on the acquired tomographic image designated based on the recognized specific part in the acquired front image of the eye.

11. The device according to claim 4, wherein the processing circuitry is further configured to
calculate a final posture of the eye based on the calculated posture of the eye and a front image of the eye acquired, via a second imaging device, along the eye axis.

12. The device according to claim 11, wherein the calculated final posture of the eye is based on a range of detection of the posture of the eye determined from the calculated posture of the eye.

13. The device according to claim 4, wherein the processing circuitry is further configured to
recognize a specific part in a front image of the eye acquired, via a second imaging device, along the eye axis,
wherein the tomographic image is acquired at a cross-sectional position designated based on of the recognized specific part in the acquired front image of the eye.

14. The device according to claim 4, wherein the processing circuitry is further configured to
recognize a surgical tool in a front image of the eye acquired, via a second imaging device, intra-operatively along the eye axis,
wherein the predetermined part in the posterior segment of the eye in the acquired tomographic image is recognized while excluding a region on the acquired tomographic image designated based on of the recognized surgical tool in the acquired front image.

15. The device according to claim 4, wherein the acquired tomographic image is at least one tomographic image selected from a plurality of tomographic images acquired, via the first imaging device, at different cross-sectional positions.

16. The device according to claim 4, wherein the processing circuitry is further configured to
generate, based on the calculated posture of the eye, guide information as for intra-operative use.

17. The device according to claim 4, wherein
the first imaging device is an optical coherence tomography device.

18. A method, comprising:
recognizing, by processing circuitry, based on a tomographic image of an eye acquired via a first imaging device, in a direction parallel to an eye axis of the eye, a predetermined part in a posterior segment of the eye; and
calculating, by the processing circuitry, a posture of the eye based on the recognized predetermined part in the posterior segment of the eye in the acquired tomographic image,
wherein the acquired tomographic image is a cross-sectional image.

19. The device according to claim 4, wherein
the calculated posture of the eye is based on a positional relationship between a depression of an optic disc of the eye and a depression of a fovea of the eye,
the depression of the optic disc of the eye and the depression of the fovea of the eye are recognized as the predetermined part in the posterior segment of the eye in the acquired tomographic image, and
the depression of the optic disc of the eye and the depression of the fovea of the eye are recognized via image recognition.

* * * * *